(12) United States Patent
McCarty et al.

(10) Patent No.: US 8,324,158 B2
(45) Date of Patent: Dec. 4, 2012

(54) METHODS FOR INHIBITING CLC-2 CHANNEL WITH GATX2

(75) Inventors: Neal McCarty, Atlanta, GA (US); Christopher H. Thompson, Atlanta, GA (US); Julia Kubanek, Decatur, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 12/373,556

(22) PCT Filed: Jul. 12, 2007

(86) PCT No.: PCT/US2007/073325
§ 371 (c)(1),
(2), (4) Date: Jan. 13, 2009

(87) PCT Pub. No.: WO2008/008873
PCT Pub. Date: Jan. 17, 2008

(65) Prior Publication Data
US 2009/0239800 A1  Sep. 24, 2009

Related U.S. Application Data

(60) Provisional application No. 60/831,110, filed on Jul. 14, 2006.

(51) Int. Cl.
*A61K 38/16* (2006.01)
*C07K 14/435* (2006.01)
*A61P 1/12* (2006.01)

(52) U.S. Cl. ........ 514/7.4; 514/21.3; 514/867; 530/324; 530/855

(58) Field of Classification Search .................. None
See application file for complete search history.

(56) References Cited

U.S. PATENT DOCUMENTS

| | | |
|---|---|---|
| 4,272,398 A | 6/1981 | Jaffe |
| 4,683,195 A | 7/1987 | Mullis et al. |
| 4,683,202 A | 7/1987 | Mullis |
| 4,861,627 A | 8/1989 | Mathiowitz et al. |
| 4,925,673 A | 5/1990 | Steiner et al. |
| 5,013,556 A | 5/1991 | Woodle et al. |
| 5,223,409 A | 6/1993 | Ladner et al. |
| 5,284,656 A | 2/1994 | Platz et al. |
| 5,288,707 A | 2/1994 | Metternich |
| 5,451,569 A | 9/1995 | Wong et al. |
| 5,494,895 A | 2/1996 | Garcia et al. |

(Continued)

FOREIGN PATENT DOCUMENTS

WO   WO 90/04036   4/1990

(Continued)

OTHER PUBLICATIONS

Cupoletti et al (2004. Am J Physiol Cell Physiol. 287: C1173-C1183).*

(Continued)

*Primary Examiner* — Zachary Howard
(74) *Attorney, Agent, or Firm* — Pabst Patent Group LLP

(57) ABSTRACT

Compositions and methods of using scorpion venom peptide that is a ligand for ClC channels are provided. One aspect provides a pharmaceutical composition containing an amount of GaTx2 effective to inhibit ClC activity. Methods of treating a disorder or symptom of a disorder related to aberrant ClC channel activity are also provided.

7 Claims, 5 Drawing Sheets

U.S. PATENT DOCUMENTS

| | | | |
|---|---|---|---|
| 5,552,534 | A | 9/1996 | Hirschmann et al. |
| 5,707,829 | A | 1/1998 | Jacobs et al. |
| 5,811,515 | A | 9/1998 | Grubbs et al. |
| 5,817,626 | A | 10/1998 | Findeis et al. |
| 5,817,879 | A | 10/1998 | Hirschmann et al. |
| 5,821,231 | A | 10/1998 | Arrhenius et al. |
| 5,874,529 | A | 2/1999 | Gilon et al. |
| 6,270,785 | B1 | 8/2001 | Selisko et al. |
| 6,593,141 | B1 | 7/2003 | Herman et al. |
| 6,689,749 | B1 | 2/2004 | Lebrun et al. |
| 6,768,002 | B1 | 7/2004 | Herrmann et al. |
| 7,176,280 | B2 | 2/2007 | Hammock et al. |
| 2002/0160454 | A1 | 10/2002 | Herrmann et al. |
| 2005/0042717 | A1 | 2/2005 | Herrmann et al. |
| 2006/0014928 | A1 | 1/2006 | Perez-Garcia et al. |

FOREIGN PATENT DOCUMENTS

| | | |
|---|---|---|
| WO | WO 90/10077 | 9/1990 |
| WO | WO 92/06204 | 4/1992 |
| WO | WO 95/06764 | 3/1995 |
| WO | WO 95/23225 | 8/1995 |
| WO | WO 97/20078 | 6/1997 |
| WO | WO 2004/056314 | 7/2004 |

OTHER PUBLICATIONS

Thompson et al (2004. Biophysical Journal. 86(1): p. 586a).*

"Dosage Form", The Free Dictionary, no date or author listed, printed on Jun. 10, 2011 from http://encyclopedia.thefreedictionary.com, 3 pages as printed.*

Lembo et al (2011. Dig Dis Sci. 56: 2639-2645).*

Abdel-Mottaleb, et al., "The first potassium channel toxin from the venom of the Iranian scorpion *Odonthobuthus doriae*", *FEBS Lett.* 580(26):6254-8 (2006). [Epub Oct. 20, 2006.]

Blanc, et al. "Solution structure of P01, a natural scorpion peptide structurally analogous to scorpion toxins specific for apamin-sensitive potassium channel", *Proteins*, 24(3):359-69 (1996).

Bowie and Sauer, "Identifying determinants of folding and activity for a protein of unknown structure", *Proc. Natl. Acad. Sci. USA*, 86(7):2152-6 (1989).

Buisine, et al., "Characterization of a new family of toxin-like peptides from the venom of the scorpion *Leiurus quinquestriatus hebraeus*. 1H-NMR structure of leiuropeptide II", *J. Pept. Res.*, 49(6):545-55 (1997).

Button, et al., "PKC-mediated stimulation of amphibian CFTR depends on a single phosphorylation consensus site. insertion of this site confers PKC sensitivity to human CFTR", *J. Gen. Physiol.*, 117(5):457-68 (2001).

Chang, et al., "Predominant interactions between μ-conotoxin Arg-13 and the skeletal muscle Na+ channel localized by mutant cycle analysis", *Biochemistry* 37, 4407-4419 (1998).

Chicchi, et al. "Purification and characterization of a unique, potent inhibitor of apamin binding from *Leiurus quinquestriatus hebraeus* venom", *J. Biol. Chem.*, 263(21):10192-7 (1988).

Fuller, et al. "State-dependent inhibition of cystic fibrosis transmembrane conductance regulator chloride channels by a novel peptide toxin", *J. Biol. Chem.*, 282(52):37545-55 (2007).

Fuller, et al., "GaTx1: A novel peptide toxin inhibitor of CFTR", *Biophys. J.* 92(6): Abstract Supplement, *51st Annual Meeting of the Biochemical Society*, 1 page (2007).

Fuller, et al., "Inhibition of CFTR channels by a peptide toxin of scorpion venom", *Am. J. Physiol. Cell. Physiol.*, 287(5):C1328-41 (2004).

Fuller, et al., "The block of CFTR by scorpion venom is state-dependent", *Biophys. J.*, 89:3960-3975 (2005).

Kharrat, et al., "Chemical synthesis and characterization of maurotoxin, a short scorpion toxin with four disulfide bridges that acts on K+ channels", Eur. J. Biochem., 242(3):491-8 (1996).

Lewis, et al., "Therapeutic potential of venom peptides", *Nature Reviews Drug Discovery*, 2:790-802 (2003).

Lopatin, et al., "Novel tools for localizing ion channels in living cells", *Trends Pharmacol. Sci.*, 19(10):395-8 (1998).

Mouhat, et al. "Contribution of the functional dyad of animal toxins acting on voltage-gated Kv1-type channels", J. Pept. Sci., 11(2):65-8 (2005).

Pusch, et al., "Pharmacological characterization of chloride channels belonging to the ClC family by the use of chiral clofibric acid derivatives", Mol. Pharmacol, 58(3):498-507 (2000).

Rodriguez, et al., "Current views on scorpion toxins specific for K+-channels", *Toxicon*, 43(8): 865-875 (2004).

Thompson, et al., "Inhibition of ClC-2 Cl- channels by a peptide component of scorpion venom", *J. Membr. Biol.*, 208:65-76 (2005).

Thompson, et al., "GaTx2: A novel peptide inhibitor of ClC-2", *Biophys. J.* 92(6): Abstract Supplement, *51st Annual Meeting of the Biochemical Society*, 1 page (2007).

Thompson, et al., "Isolation and characterization of a high affinity peptide inhibitor of ClC-2 chloride channels", *J. Biol. Chem.*, 284(38):26051-26062;S1-S8 (2009).

Zerrouk, et al., "Characterization of PO1, a new peptide ligand of the apamin-sensitive Ca2+ activated K+ channel", *Int. J. Pept. Protein Res.*, 48(6):514-21 (1996).

Bernstein, "Antivenom (Scorpion and Spider)" , Goldfranks Toxicologic Emergencies, Chaper 115A (2010).

Cortez et al., 2010. Disruption of ClC-2 expression is associated with progressive neurodegeneration in aging mice. Neuroscience 167(1):154-162.

Edwards et al., 2010. Photoreceptor degeneration, azoospermia, leukoencephalopathy, and abnormal RPE cell function in mice expressing an early stop mutation in CLCN2. Invest Ophthalmol Vis Sci. 51(6):3264-72.

Everett et al., 2007. Linkage and mutational analysis of CLCN2 in childhood absence epilepsy. Epilepsy Res. 75(2-3):145-53.

Galanopoulou, A.S. 2010. Mutations affecting GABAergic signaling in seizures and epilepsy. Pflugers Arch. 460(2):505-23.

Lacy and Chey, 2009. Lubiprostone: chronic constipation and irritable bowel syndrome with constipation. Expert Opin Pharmacother. 10(1):143-52.

Medina et al., 2008. Novel mutations in Myoclonin1/EFHC1 in sporadic and familial juvenile myoclonic epilepsy.Neurology 70(22 Pt 2):2137-44.

Rinke et al., 2010. ClC-2 voltage-gated channels constitute part of the background conductance and assist chloride extrusion. J. Neurosci. 30(13):4776-86.

Romanenko et al., 2008. Clcn2 encodes the hyperpolarization-activated chloride channel in the ducts of mouse salivary glands. Am J Physiol Gastrointest Liver Physiol. 295(5):G1058-67.

Insert from Scorpion Anticienom, Refined equine antiscorpion serum globulins, Jun. 1990.

Stogmann et al., 2006. Mutations in the CLCN2 gene are a rare cause of idiopathic generalized epilepsy syndromes. Neurogenetics 7(4):265-8.

* cited by examiner

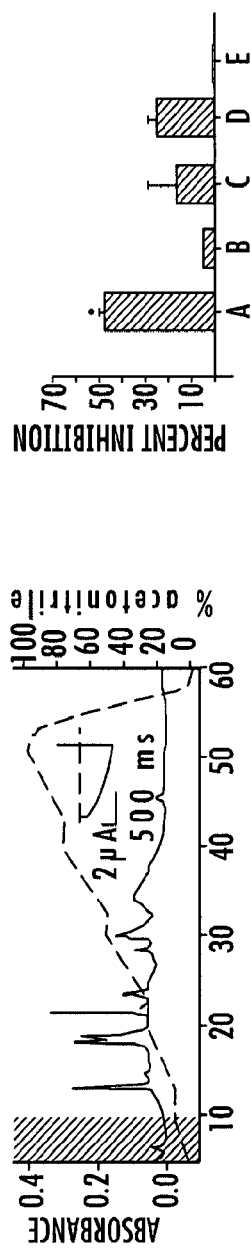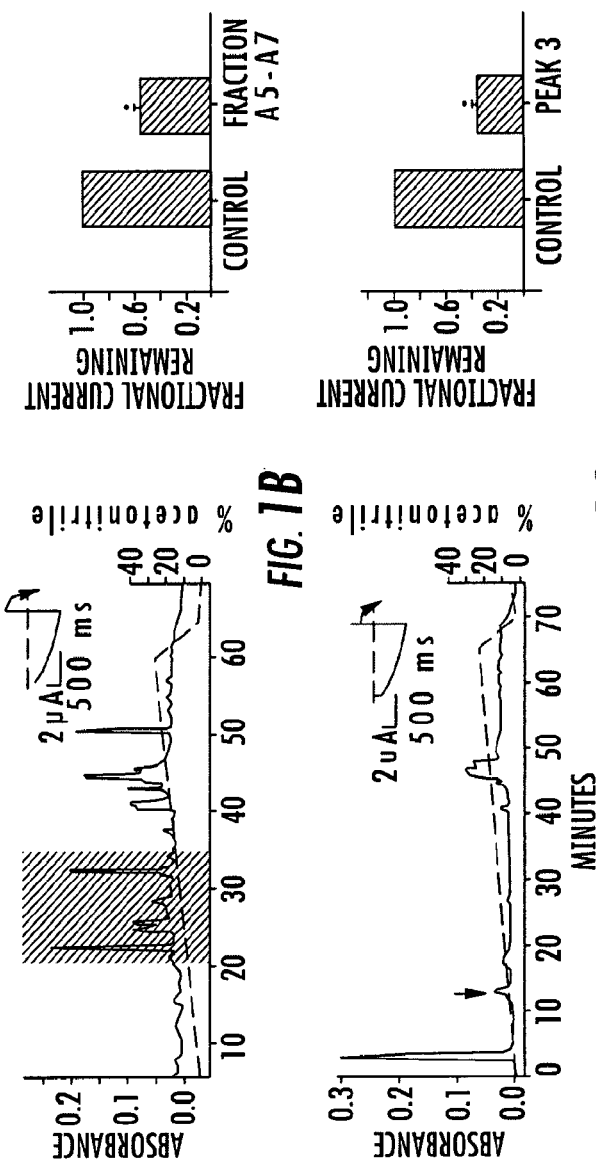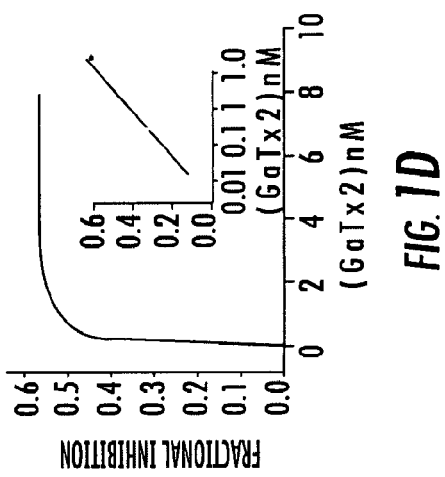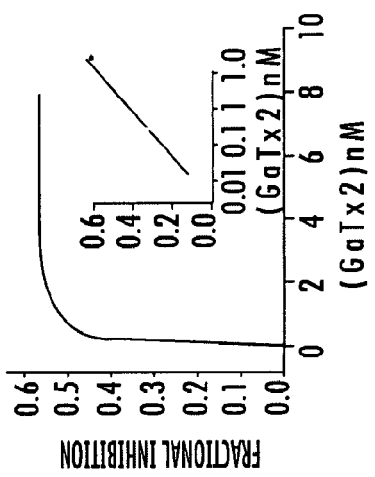
FIG. 1A
FIG. 1B
FIG. 1C
FIG. 1D

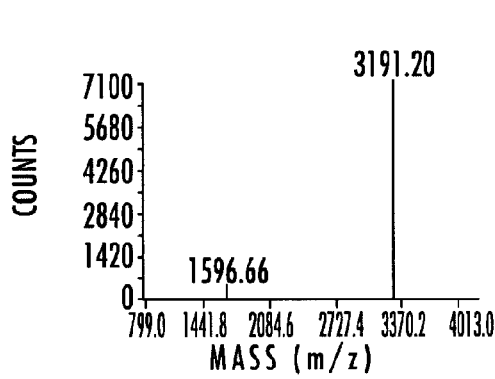

FIG. 2A

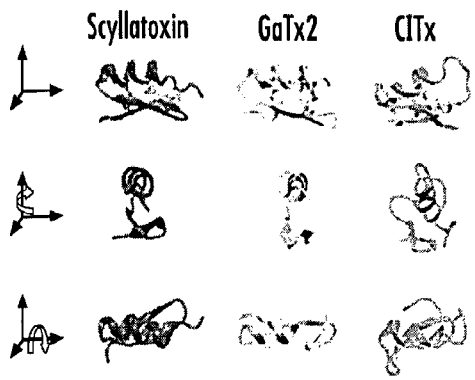

FIG. 2C

| NAME | SEQUENCE | PERCENT IDENTITY |
|---|---|---|
| | ttt     aaaaaaaaatt   ttBBBBttBBBBttt | |
| GaTx2 | V S C ..... E D C P D H C S T Q K ... A R A K C D N D K C V C E P I | -- |
| LEIUROPEPTIDE II | V S C ..... E D C P D H C S T Q K ... A R A K C D N D K C V C E P I | 100 |
| LEIUROPEPTIDE III | V S C ..... E D C P D H C S T Q K ... A R A K C D N D K C V C E P K | 96 |
| NEUROTOXIN P01 | V S C ..... E D C P E H C S T Q K ... A Q A K C D N D K C V C E P I | 93 |
| OdK1 | V S C ..... E D C P E H C S T Q K ... A R A K C D N D K C V C E S V | 89 |
| LEIUROPEPTIDE I | V G C ..... E E C P M H C K G K N ... A K P T C D N G V C N C N V | 46 |
| MAUROTOXIN | V S C T G S K D C Y A P C R K Q T G C P N A K C I N K S C K C Y G C | 27 |
| SCYLLATOXIN | A F C N .. L R M C Q L S C R S L G ..... L L G K C I G D K C E C V K H | 27 |

FIG. 2B

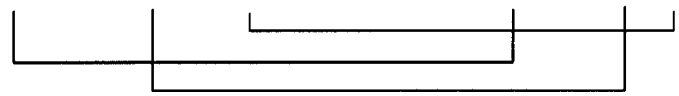

CONTROL

+2 nM SYNTHETIC GaTx2

FIG. 3A

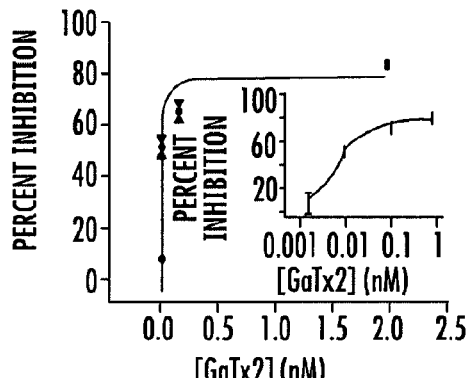

FIG. 3B

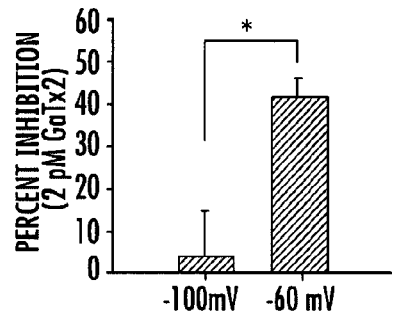

FIG. 3C

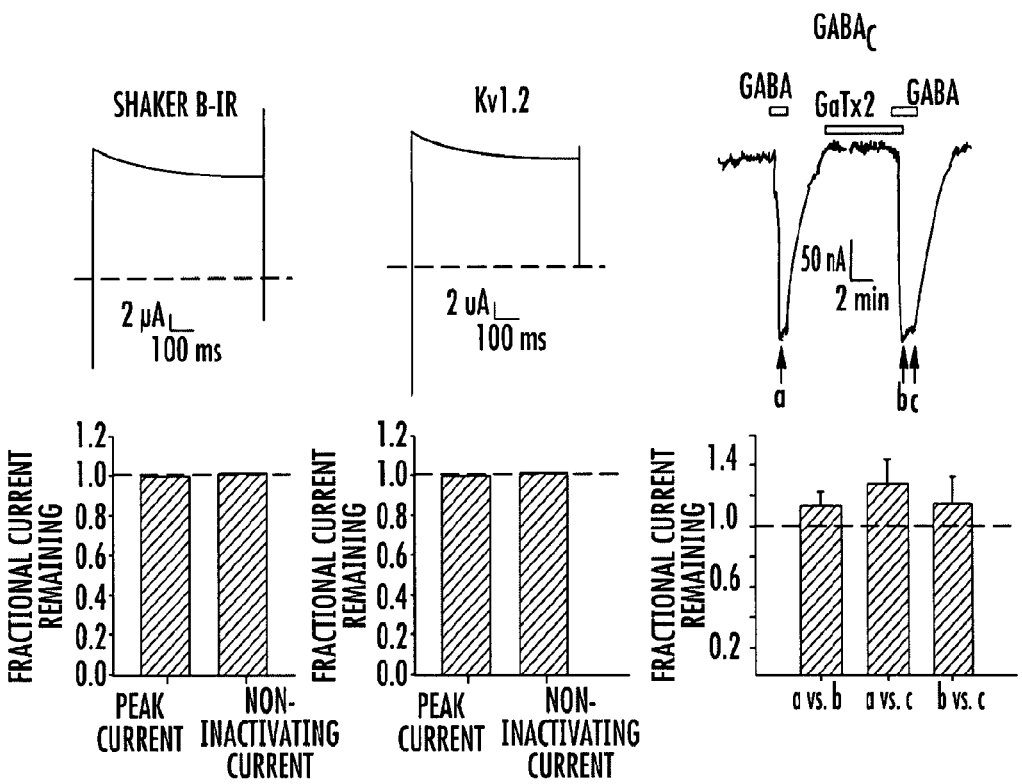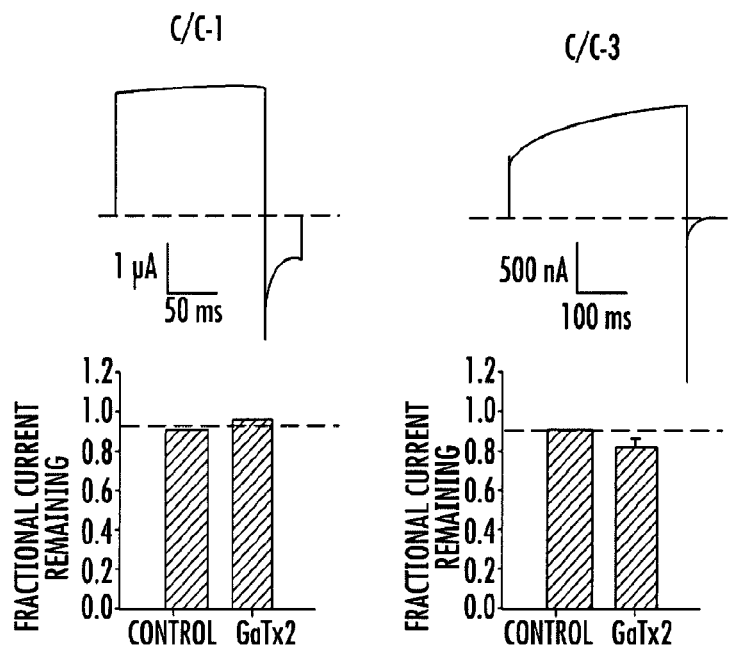

METHODS FOR INHIBITING CLC-2 CHANNEL WITH GATX2

CROSS-REFERENCE TO RELATED APPLICATION

This application is a filing under 35 U.S.C. §371 of PCT/US2007/073325 filed with the U.S. Receiving Office of the Patent Cooperation Treaty on Jul. 12, 2007, and claims priority to and benefit of U.S. Provisional Patent Application No. 60/831,110 filed on Jul. 14, 2006, by Nael McCarty, Christopher H. Thompson, and Julia Kubanek, and where permissible is incorporated herein in their entirety.

STATEMENT REGARDING FEDERALLY SPONSORED RESEARCH OR DEVELOPMENT

This invention was made with Government Support under Agreement 1 R21 DK066409-01 award to Nael McCarty by the National Institutes of Health; Agreement MCB-0224690 awarded to Nael McCarty by the National Science Foundation; and Agreement MCCART06P0 awarded to Nael McCarty by the Cystic Fibrosis Foundation. The Government has certain rights in the invention.

REFERENCE TO SEQUENCE LISTING

The Sequence Listing submitted Apr. 24, 2012 as a text file named "GTRC_3913.ST25.txt," created on Jun. 28, 2010 and having a size of 4,025 bytes is hereby incorporated by reference pursuant to 37 C.F.R. §1.52(e)(5).

FIELD OF THE INVENTION

Aspects of the invention are generally related to compositions and methods of modulating chloride channel activity, for example using peptide ligands isolated from scorpion venom.

BACKGROUND OF THE INVENTION

Chloride-conducting ion channels of the ClC family have important roles in a host of biological processes. These polytopic membrane proteins form aqueous pathways through which anions are selectively allowed to pass down their concentration gradients. The ClCs are found in nearly all organisms, with members in every mammalian tissue, yet relatively little is known about their mechanism or regulation. It is clear, however, that they are fundamentally different in molecular construction and mechanism from the well-known potassium-, sodium-, and calcium-selective channels.

ClC channels play roles as diverse as cell volume regulation, renal salt reabsorption, controlling resting potential in excitable cells, and regulation of endosomal pH. Some ClCs are broadly expressed; therefore, their disruption by mutation or knockout can have serious physiological consequences. For example, all but one of the nine ClC family members is expressed in the kidney. A Cl⁻ channel gene is the locus of the primary defect in several human diseases. Mutations in genes encoding ClC channels are involved in generalized epilepsy, Bartter's syndrome, Dent's disease (a form of bone disorder due to improper handling of calcium by the kidney), myotonia, and osteopetrosis. Despite their central roles in many physiological processes, our understanding of the structures and mechanisms of anion-permeable channels has lagged far behind that of their cation-permeable peers. One clear reason for this discrepancy is a paucity of specific probes that may be useful as tools for studying the permeation pathways and/or gating mechanisms of anion channels.

Venoms from snakes, scorpions, marine snails, and spiders are rich sources of peptide ligands that have proven to be of great value in the functional exploration of cation channels. Peptide ligands have proven to be among the most potent and selective antagonists available for voltage-gated channels permeable to $K^+$, $Na^+$, and $Ca^{2+}$, and have been very useful tools for detailed structural analysis of these proteins. Pore-blocking toxins provide clues about the arrangement of channel domains, about the interactions between the permeant ions and the pore, and about the proximity and interactions of the gating machinery with the pore. Gating modifiers provide tools to dissect the processes underlying the transitions between gating states. Peptide ligands have high potential as lead compounds for the development of therapeutics targeting pain, diabetes, multiple sclerosis, cardiovascular diseases, and cancer. Because peptide ligands have well-defined structures, constrained by disulfide bridges, they bind with much higher affinity and specificity than other blockers available to date, and report the structures of their targets at molecular detail. Unfortunately, no peptide toxins have been isolated that inhibit a ClC channel.

Therefore, it is an object to provide ClC channel ligands and methods of their use.

It is another object to provide peptide compositions that block or inhibit Cl⁻ channels.

It is yet another object to provide peptide compositions that block or inhibit Cl⁻ channels for the manufacture of a medicament.

It is another object to provide pharmaceutical peptide compositions for modulating chloride ion channels.

It is still another object to provide methods for treating ClC channel-related disorders with peptide inhibitors of ion channels.

SUMMARY OF THE INVENTION

Compositions containing ClC channel ligands and methods of their use are provided. In one aspect, the ClC channel ligand is a scorpion venom peptide having at least 97%, 98%, 99% or 100% sequence identity to [1]VSCEDCPDHC-STQKARAKCDNDKCVCEPI[29] (SEQ ID NO: 1)(also referred to as GaTx2). Variants and derivatives of the peptide ligand are also provided. The peptide ligand is believed to have a molecular mass of about 3.2 kDa and $K_D$ of about 12 µM for ClC-2 at −100 mV.

In another aspect, the peptide ligand is isolated from *Leiurus quinquestriatus hebraeus* venom.

Still another aspect provides a method for reducing ClC channel activity by contacting the ClC channel with the disclosed ClC channel ligands.

Still another aspect provides a method of reducing chloride transport through a chloride channel by contacting the chloride channel with the polypeptide ligand.

Yet another aspect provides a method for treating a disorder or symptoms of a disorder related to aberrant chloride channel activity by administering a therapeutically effective amount of the polypeptide ligand. The disorder can be selected from the group consisting of cancer, cystic fibrosis, epilepsy, renal tubular disorders, Bartter's syndrome, Dent's disease, myotonia, osteopetrosis, Angleman or Prader-Willi, upregulation of chloride channels in glioma cells, diarrhea-predominant inflammatory bowel syndrome, autosomal

BRIEF DESCRIPTION OF THE DRAWINGS

FIGS. 1A-D show representative (reversed phase) RP-HPLC chromatograms of Lqh pf-venom (partially-fractionated venom) (A) or active fractions (B, C). The area included in the gray boxes, or indicated by an arrow, contains the active fraction or peak. The elution gradient is represented by a dashed line. The right panel presents summary data for fraction activity. Bars show mean±SEM for 3-10 observations. The inset shows representative traces from Two-electrode Voltage Clamp (TEVC) experiments in the absence (black trace) or presence (gray trace) of the active fractions or isolated peak at $V_M=-160$ mV following a step from $-30$ mV. (D). Dose-response curve from a single TEVC experiment for inhibition of ClC-2 at $V_M=-160$ mV by 0.01, 0.1, 1, or 10 nM native toxin. Inset shows dose-response plotted on a log scale.

FIG. 2A is a line graph showing MALDI-MS analysis of peak 3.

FIG. 2B shows the sequence alignment of GaTx2 (SEQ ID NO:1) with other previously identified, highly related toxins (Leiuropeptide II (SEQ ID NO:6), Leiuropeptide III (SEQ ID NO:7), Neurotoxin PO1 (SEQ ID NO:8), OdK1 (SEQ ID NO:9), Leiuropeptide I (SEQ ID NO:10), Maurotoxin (SEQ ID NO:11 and Scyllatoxin (SEQ ID NO:12). Disulfide bridge connectivity (specifically for GaTx2) is shown below the sequence alignment, while the predicted secondary structure for GaTx2 is shown above the sequence.

FIG. 2C shows a homology model of GaTx2 (middle) with the NMR structures of Scyllatoxin (left) and Chlorotoxin (right), in three orientations. The top panel shows disulfide bridges in bond representation.

FIG. 3A is a multi-channel inside-out patch recording at $V_M=-100$ mV of ClC-2 in the presence of control extracellular solution (top), or 2 nM synthetic GaTx2 (bottom). The record at the left is from the beginning of the experiment, while the record at the right is from the end of the experiment, after the backfilled toxin had some time to diffuse to the patch at the tip of the electrode.

FIG. 3B is a dose-response curve for inhibition of ClC-2 currents from multi-channel patches by GaTx2 at concentrations of 2 pM, 20 pM, 200 pM, and 2 nM; $V_M=-100$ mV. All points contain data from 6-17 measurements of window current at each concentration.

FIG. 3C is a bar graph showing a comparison of inhibition of ClC-2 by 2 pM GaTx2 when currents were measured at $V_M=-60$ or $-100$ mV, in multichannel patches as shown in FIG. 3A; * indicated p<0.001.

FIGS. 6A and 6B show line graphs and bar graphs of current data showing that GaTx2 does not inhibit ShB-IR K$^+$ channel currents, Kv1.2 K$^+$ channel currents, or currents mediated by GABA$_C$ receptor, ClC-1, or ClC-3 chloride channels.

FIG. 6C shows line graphs and bar graphs of GABA current data in the absence and presence of GaTx2. Comparison of current in the presence of 10 μM GABA to currents in the presence of 10 μM GABA plus 10 nM CGaTx2 showed no change (13±9.4% increase, p=0.32). GABA-induced Cl$^-$ currents also did not increase upon removal of toxin from the bath solution (14±19% increase, p=0.74). This suggests that GaTx2 is not capable of inhibiting currents from GABA$_C$ receptors.

FIG. 6D shows line graphs and bar graphs of ClC-1 current data no inhibition of ClC-1 in the absence and presence of GaTx2. In the presence of 10 nM GaTx2, tail currents at $V_M=-120$ mV from +60 mV were 1.036±0.012 fold larger than currents after washout of toxin, implying no inhibition of ClC-1.

FIG. 6E shows line graphs and bar graphs of ClC-3 current data in the absence and presence of GaTx2. 10 nM GaTx2 did not inhibit ClC-3 channel mediated currents.

DETAILED DESCRIPTION OF THE INVENTION

I. Definitions

Figure 4A:
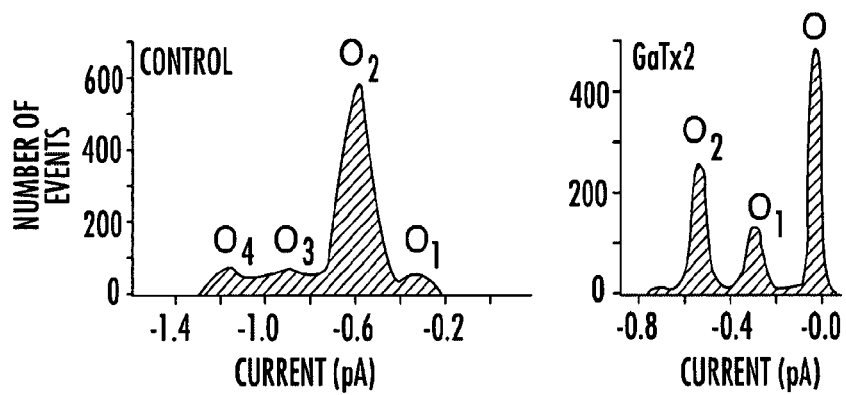
FIG. 4A is a line graph of current versus number of events and shows GaTx2 does not change single-channel amplitude. All-points amplitude histograms in the absence (left) and presence (right) of 2 nM GaTx2.
Figure 4B:
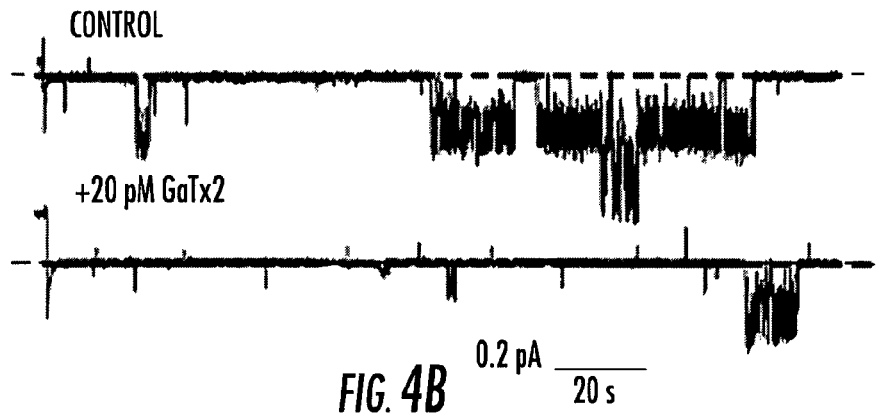
FIG. 4B shows a representative single channel trace of ClC-2 with and without 20 μM synthetic toxin at $V_M=-100$ mV.

The term "antibody" includes complete antibodies, as well as fragments thereof (e.g., F(ab')$_2$, Fab, etc.) and modified antibodies produced therefrom (e.g., antibodies modified through chemical, biochemical, or recombinant DNA methodologies), with the proviso that the antibody fragments and modified antibodies retain antigen binding characteristics sufficiently similar to the starting antibody so as to provide for specific detection of antigen.

By "antisense polynucleotide" is meant a polynucleotide having a nucleotide sequence complementary to a given polynucleotide sequence including polynucleotide sequences associated with the transcription or translation of the given polynucleotide sequence (e.g., a promoter), where the antisense polynucleotide is capable of hybridizing to a polynucleotide sequence. Of particular interest are antisense polynucleotides capable of inhibiting transcription and/or translation, either in vitro or in vivo.

By "antivenom" is meant an antivenin or an antitoxin to a venom; or an antiserum containing such antitoxin.

The term "biologically active" refers to ClC channel ligands having structural, regulatory, or biochemical functions of a naturally occurring polypeptide. Likewise, "immunologically active" defines the capability of the natural, recombinant or synthetic ClC channel ligand, or any oligopeptide thereof, to induce a specific immune response in appropriate animals or cells and to bind with specific antibodies.

The term "ClC channel ligand" refers to a molecule or compound that interacts with a ClC channel. An exemplary ClC channel ligand includes a polypeptide having at least 97% sequence identity to SEQ ID NO: 1. The terms "scorpion venom polypeptide", "peptide toxin", "GaTx2", and "ClC channel ligand" are used interchangeably. The mammalian ClC family includes nine members including ClC-0, CC-1, ClC-2, ClC-3, ClC-4, ClC5, ClC-6, ClC-K1, and ClC-K2.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

The term "derivative" as used herein refers to the chemical modification of a ClC channel ligand. Illustrative of such modifications would be replacement of hydrogen by an alkyl, acyl, or amino group. A polypeptide derivative would retain essential biological characteristics of a natural polypeptide.

The term "effective amount" or "therapeutically effective amount" means a dosage sufficient to provide treatment of the disease state being treated or to otherwise provide a desired pharmacologic and/or physiologic effect. The precise dosage will vary according to a variety of factors such as subject-dependent variables (e.g., age, immune system health, etc.), the cause of the injury (e.g., the species of scorpion), the disease (e.g., the nature of the effect on ClC channels caused by the disease), and the treatment being effected. In the case of a scorpion sting, an "effective amount" is that amount necessary to substantially improve the likelihood of treating the sting, in particular that amount which improves the likelihood of successfully preventing effects of the toxins on the subject, relieving or minimizing toxin effects, or arresting any complications caused or exacerbated by the toxin. Where the scorpion toxin is used as an insecticide or pesticide, an "effective amount" is that amount necessary to kill the insect or pest, or otherwise affect the behavior of the insect or pest in such a way that it no longer performs or causes undesired events or activities, e.g. consume or damage plants.

By "envenomation" is meant when a subject is bitten or stung by a scorpion.

The terms "individual," "host," "subject," and "patient" are used interchangeably herein, and refer to a mammal, including, but not limited to, murines, simians, humans, mammalian farm animals, mammalian sport animals, and mammalian pets.

As used herein the term "isolated" is meant to describe a compound of interest (e.g., either a polynucleotide or a polypeptide) that is in an environment different from that in which the compound naturally occurs e.g. separated from its natural milieu such as by concentrating a peptide to a concentration at which it is not found in nature. "Isolated" is meant to include compounds that are within samples that are substantially enriched for the compound of interest and/or in which the compound of interest is partially or substantially purified.

"Polypeptide" as used herein refers to an oligopeptide, peptide, modified polypeptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule, but is meant to encompass analogues, degenerate substitutions, etc.

"Polynucleotide" and "nucleic acid" as used interchangeably herein refer to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "polynucleotide" or "nucleic acid" is used to refer to a specific polynucleotide sequence (e.g. encoding a scorpion toxin such as GaTx2), the terms are meant to encompass polynucleotides that encode a polypeptide that is functionally equivalent to the recited polypeptide, e.g., polynucleotides that are degenerate variants, or polynucleotides that encode biologically active variants or fragments of the recited polypeptide.

As used herein, the term "prodrug" refers to an active agent chemically transformed into a per se inactive derivative which, by virtue of chemical or enzymatic attack, is converted to the parent agent within the body before or after reaching the site of action. Prodrugs are frequently (though not necessarily) pharmacologically inactive until converted to the parent drug. A prodrug may be converted into the parent drug by various mechanisms, including enzymatic processes and metabolic hydrolysis. Examples of prodrugs include, but are not limited to, ester and amide prodrugs; polyethylene glycol prodrugs (with and without a linker); N-acyl amine prodrugs, dihydropyridine prodrugs, 2-hydroxybenzamide prodrugs; carbamate prodrugs; peptide prodrugs; Mannich bases, and Schiff bases.

"Protein Transduction Domain" or PTD refers to a polypeptide, polynucleotide, carbohydrate, or organic or inorganic compounds that facilitates traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle. Exemplary PTDs include but are not limited to HIV TAT YGRKKRRQRRR (SEQ. ID NO:2) or RKKRRQRRR (SEQ. ID N0.3); 11 Arginine residues, or positively charged polypeptides or polynucleotides having 8-15 residues, preferably 9-11 residues.

"Subjects" or "patients" as used herein, encompasses any subject or patient amenable to application of the methods of treatment or diagnostic methods. Mammalian subjects and patients, particularly human subjects or patients, are of particular interest.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

As used herein, the terms "treatment," "treating," and the like, refer to obtaining a desired pharmacologic and/or physiologic effect. The effect may be prophylactic in terms of completely or partially preventing a symptom thereof and/or may be therapeutic in terms of a partial or complete cure for an adverse affect attributable to the condition. "Treatment," as used herein, covers any treatment of an injury in a mammal, particularly in a human, and includes: (a) preventing the injury, arresting any complications, and minimizing its effects; (b) relieving the symptoms; (c) preventing the disease from occurring in a subject which may be predisposed to the disease but has not yet been diagnosed as having it; (d) inhibiting the disease, i.e., arresting its development; and (e) relieving the disease, i.e., causing regression of the disease.

A "substantial portion" of an amino acid or nucleotide sequence refers to an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification involves amino acid and nucleotide sequences encoding polypeptides that comprise one or more particular scorpion toxin proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

As used herein, "substantially similar" refers to nucleic acid fragments wherein changes in one or more nucleotide bases results in substitution of one or more amino acids, but do not affect the functional properties of the polypeptide encoded by the polynucleotide sequence. "Substantially similar" also refers to modifications of the nucleic acid fragments of the instant invention such as deletion or insertion of one or more nucleotides that do not substantially affect the functional properties of the resulting protein molecule. It is therefore understood that the invention encompasses more than the specific exemplary sequences.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) *Nucleic Acid Hybridisation*, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95%, 98%, 99% or more identical to the amino acid sequences reported herein.

II. ClC Channel Ligands

A. Peptide Ligands

It has been discovered that the toxin referred to as GaTx2 binds to ClC channels and modulates chloride channel activity. GaTx2 was previously believed to be a $K^+$ channel ligand based on homology to other toxins. One embodiment provides a toxin that has at least 97%, 98%, 99% or 100% sequence identity to VSCEDCPDHCSTQKARAKCDND-KCVCEPI (SEQ ID NO: 1) a variant, derivative or prodrug thereof. GaTx2 is approximately a 3.2 kDa peptide with three disulfide bonds which hold together a secondary structure likely to be composed of one α-helix and two β-strands. GaTx2 has an apparent dissociation constant of about 12 μM for ClC-2 at −100 mV.

GaTx2 inhibits ClC-2 with higher affinity than any other available drug and, in fact, is the best inhibitor of any chloride channel. The previously best available ClC inhibitor, CPP, interacts with ClC-1 with a $K_D$ of 15 μM, while GaTx1 inhibits CFTR with a $K_D$ of 25 nM at −100 mV (Fuller, M. D., et al. (2007) *Biophys. J.* 92 Supplement, 275a, Abstract).

The physiological role of ClC-2 is still largely undefined. It is thought that ClC-2 may play a role in vascular smooth muscle cells and may be expressed on the apical membrane of epithelial cells along with CFTR, although this is still controversial. GaTx2 will be useful in determining the role of ClC-2 in these cells and may aid in determining the membrane localization of ClC-2 in specific cell types. Also, mutations in ClC-2 have been implicated in epilepsy, while underactivity of WT ClC-2 has been implicated in constipation-associated inflammatory bowel disease, Therefore, GaTx2 may serve as a lead compound for peptidomimetic drugs that target ClC-2.

GaTx2 was isolated from the venom of *Leiurus quinquestriatus hebraeus*, the giant Israeli scorpion. The peptide ligand binds to ClC channels, in particular chloride channels. In one embodiment, the ClC channel is ClC-2.

Another embodiment provides a purified peptide isolated from the venom of *Leiurus quinquestriatus hebraeus* wherein the peptide interacts with chloride channels in a voltage dependent manner.

B. Variants of ClC Channel Ligands

1. Conservative Substitutions of Amino Acids

Another embodiment provides nucleic acid molecules that encode a polypeptide having a conservative amino acid change, compared with SEQ ID NO: 1. For example, variants can be obtained that contain one or more amino acid substitutions of SEQ ID NO: 1, in which an alkyl amino acid is substituted for an alkyl amino acid in a GaTx2 amino acid sequence, an aromatic amino acid is substituted for an aromatic amino acid in a GaTx2 amino acid sequence, a sulfur-containing amino acid is substituted for a sulfur-containing amino acid in a GaTx2 amino acid sequence, a hydroxy-containing amino acid is substituted for a hydroxy-containing amino acid in a GaTx2 amino acid sequence, an acidic amino acid is substituted for an acidic amino acid in a GaTx2 amino acid sequence, a basic amino acid is substituted for a basic amino acid in a GaTx2 amino acid sequence, or a dibasic monocarboxylic amino acid is substituted for a dibasic monocarboxylic amino acid in a GaTx2 amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the disclosed peptide ion channel inhibitors. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Particular variants of GaTx2 are characterized by having at least 70%, at least 80%, at least 90%, at least 95% or greater than 96% sequence identity to the corresponding amino acid sequence (e.g., SEQ ID NO:1), wherein the variation in amino acid sequence is due to one or more conservative amino acid substitutions.

"Conservative amino acid" variants can be obtained by oligonucleotide-directed mutagenesis, linker-scanning mutagenesis, mutagenesis using the polymerase chain reaction, and the like (see Ausubel (1995) at pages 8-10 to 8-22; and McPherson (ed.), *Directed Mutagenesis: A Practical Approach* (IRL Press 1991)). A variant GaTx2 polypeptide can be identified by the ability to specifically bind anti-GaTx2 antibodies.

2. Variants Containing Non-naturally Occurring Amino Acid Residues

The disclosed peptide ligands can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci*. USA 90:10145 (1993).

In a second method, translation is carried out in *Xenopus oocytes* by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

3. Non-Conservative Amino Acid Substitutions

A limited number of nonconservative amino acids, amino acids that are not encoded by the genetic code, non-naturally occurring amino acids, and unnatural amino acids may be substituted for GaTx2 amino acid residues.

Essential amino acids in the polypeptides can be identified according to procedures known in the art, such as site-directed mutagenesis or alanine-scanning mutagenesis (Cunningham and Wells, *Science* 244:1081 (1989), Bass et al., *Proc. Nat'l Acad. Sci*. USA 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity to identify amino acid residues that are critical to the activity of the molecule. See also, Hilton et al., *J. Biol. Chem.* 271:4699 (1996).

Although sequence analysis can be used to further define the GaTx2 anion channel binding region, amino acids that play a role in GaTx2 binding activity (such as binding of GaTx2 to ClC-2, or to an anti-GaTx2 antibody) can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306 (1992), Smith et al., *J. Mol. Biol.* 224:899 (1992), and Wlodaver et al., *FEBS Lett.* 309:59 (1992).

Multiple amino acid substitutions can be made and tested using known methods of mutagenesis and screening, such as those disclosed by Reidhaar-Olson and Sauer (*Science* 241:53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)). Moreover, GaTx2 labeled with biotin or FITC can be used for expression cloning of GaTx2 ligands.

Variants of nucleic acids encoding GaTx2 polypeptide (SEQ ID NO: 1) can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-GaTx2 antibodies, can be recovered from the host cells and rapidly sequenced using modern equipment. These methods allow the rapid determination of the importance of individual amino acid residues in a polypeptide of interest, and can be applied to polypeptides of unknown structure.

4. Fragments of ClC Channel Ligands

Another embodiment provides "functional fragments" of GaTx2 polypeptides and nucleic acid molecules encoding such functional fragments. Routine deletion analyses of nucleic acid molecules can be performed to obtain functional fragments of a nucleic acid molecule that encodes a GaTx2 polypeptide. As an illustration, DNA molecules can be digested with Bal31 nuclease to obtain a series of nested deletions. The fragments are then inserted into expression vectors in proper reading frame, and the expressed polypeptides are isolated and tested for the ability to bind anti-GaTx2 antibodies. One alternative to exonuclease digestion is to use oligonucleotide-directed mutagenesis to introduce deletions or stop codons to specify production of a desired fragment. Alternatively, particular fragments of a GaTx2 gene can be synthesized using the polymerase chain reaction.

This general approach is exemplified by studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological Interferon Systems*, Proceedings of ISIR-TNO Meeting on Interferon Systems, Cantell (ed.), pages 65-72 (Nijhoff 1987), Herschman, "The EGF Receptor," in *Control of Animal Cell Proliferation*, Vol. 1, Boynton et al., (eds.) pages 169-199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

Another embodiment provides functional fragments of a GaTx2 gene that have amino acid changes, compared with SEQ ID NO:1. A variant GaTx2 gene can be identified on the basis of structure by determining the level of identity with disclosed nucleotide and amino acid sequences, as discussed above. An alternative approach to identifying a variant gene on the basis of structure is to determine whether a nucleic acid molecule encoding a potential variant GaTx2 gene can hybridize to a nucleic acid molecule comprising a nucleotide sequence.

One embodiment provides polypeptide fragments or peptides having an epitope-bearing portion of a GaTx2 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81.3998 (1983)).

In contrast, polypeptide fragments or peptides may include an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides can contain at least four to ten amino acids, at least ten to fifteen amino acids, or about 15 to about 30 amino acids of an amino acid sequence disclosed herein. Such epitope-bearing peptides and polypeptides can be produced by fragmenting a GaTx2 polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology*, pages 9.3.1-9.3.5 and pages 9.4.1-9.4.11 (John Wiley & Sons 1997).

For any GaTx2 polypeptide, including variants and fusion proteins, one of ordinary skill in the art can readily generate a fully degenerate polynucleotide sequence encoding that variant. Moreover, those or skill in the art can use standard software to devise GaTx2 variants based upon the nucleotide and amino acid sequences described herein. Accordingly, the present invention includes a computer-readable medium encoded with a data structure that provides at least one of the following sequences: SEQ ID NO:1. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

B. Peptidomimetics

Another embodiment provides peptidomimetics of the ClC channel ligands, for example SEQ ID NO: 1. Peptidomimetics, as used herein, refers to molecules bearing identifiable resemblance to the scorpion venom polypeptide, for example SEQ ID NO: 1 that, as a ligand of a chloride channel, can imitate or inhibit the effect of the scorpion venom polypeptide. Exemplary ClC channel ligand peptidomimetics have increased bioavailability, biostability, bioefficiency, and/or bioselectivity against the biological target of the parent peptide, for example ClC-2.

Examples of peptidomimetics have been isolated as natural products, synthesized as libraries from novel subunits, and designed on the basis of X-ray crystallographic studies and through an intricate knowledge of the biological mode of action of natural peptides. Examples of such peptidomimetic materials are described in Moore et al., *Chem. Rev.* 101(2), 3893-4012 (2001).

Peptidomimetics that structurally and/or functionally resemble a polypeptide embodiment may be made. Several approaches to make peptidomimetics that resemble polypeptides have been described (see, e.g., U.S. Pat. Nos. 5,288,707; 5,552,534; 5,811,515; 5,817,626; 5,817,879; 5,821,231; and 5,874,529).

Peptidomimetic materials of the disclosed ClC channel ligands can be generated to fall within one of four categories of known peptidomimetics: α-peptides, β-peptides, γ-peptides, and δ-peptides. Copolymers of these peptides can also be used.

Examples of α-peptide peptidomimetics include, but are not limited to, N,N'-linked oligoureas, oligopyrrolinones, oxazolidin-2-ones, azatides and azapeptides.

Examples of β-peptides include, but are not limited to, β-peptide foldamers, α-aminoxy acids, sulfur-containing β-peptide analogues, and hydrazino peptides.

Examples of γ-peptides include, but are not limited to, γ-peptide foldamers, oligoureas, oligocarbamates, and phosphodiesters.

Examples of δ-peptides include, but are not limited to, alkene-based δ-amino acids and carbopeptoids, such as pyranose-based carbopeptoids and furanose-based carbopeptoids.

Other peptidomimetics of the ClC channel ligands can be oligomers having backbones which can adopt helical or sheet conformations. Example of such compounds include, but are not limited to, compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination.

Examples of compounds containing backbones utilizing bipyridine segments include, but are not limited to, oligo (pyridine-pyrimidines), oligo(pyridine-pyrimidines) with hydrazal linkers, and pyridine-pyridazines.

Examples of compounds containing backbones utilizing solvophobic interactions include, but are not limited to, oligoguanidines, aedamers (structures which take advantage of the stacking properties of aromatic electron donor-acceptor interactions of covalently linked subunits) such as oligomers containing 1,4,5,8-naphthalene-tetracarboxylic diimide rings and 1,5-dialkoxynaphthalene rings, and cyclophanes such as substituted N-benzyl phenylpyridinium cyclophanes.

Examples of compounds containing backbones utilizing side chain interactions include, but are not limited to, oligothiophenes such as olihothiophenes with chiral p-phenyloxazoline side chains, and oligo(m-phenylene-ethynylene)s.

Examples of compound containing backbones utilizing hydrogen bonding interactions include, but are not limited to, aromatic amide backbones such as oligo(acylated 2,2'-bipyridine-3,3'-diamine)s and oligo(2,5-bis[2-aminophenyl] pyrazine)s, diaminopyridine backbones templated by cyanurate, and phenylene-pyridine-pyrimidine ethynylene backbones templated by isophthalic acid.

Examples of compounds containing backbones utilizing metal coordination include, but are not limited to, zinc bilinones, oligopyridines complexed with Co(II), Co(III), Cu(II), Ni(II), Pd(II), Cr(III), or Y(III), oligo(m-pheylene ethynylene)s containing metal-coordinating cyano groups, and hexapyrrins.

C. Vectors and Nucleic Acids Encoding ClC Channel Ligands

Another embodiment provides nucleic acid compositions that may encode all or a biologically active part of GaTx2, e.g. the nucleic acids may encode all or part of SEQ ID NO: 1, and may be synthesized oligonucleotides, mRNA, cDNA, or genomic DNA. These polynucleotides can be used, when in a recombinant expression vector, to produce the encoded GaTx2 or functional fragment thereof. They are also useful as hybridization probes in methods of detecting scorpion venom toxins gene expression, specifically transcription. Accordingly, one embodiment provides recombinant vectors and host cells containing a polynucleotide encoding GaTx2.

Another embodiment provides polynucleotides coding for a scorpion venom toxin polypeptide sequence set forth in SEQ ID NO: 1 an identifying sequence thereof. An "identifying sequence" is a contiguous sequence of residues at least about 10 nucleotides (nt) to about 20 nt in length, usually at least about 40 nt to about 55 nt in length, that uniquely identifies the provided sequence. Encompassed in the term "scorpion venom toxin-encoding polynucleotide" are polynucleotides comprising about 10, 20, 25, 50, 72 contiguous nucleotides coding for SEQ ID NO: 1.

"Hybridization" refers to the association of two nucleic acid sequences to one another by hydrogen bonding. Two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook, et al., *Molecular Cloning: A Laboratory Manual,* 2nd Ed. (1989), Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated $T_m$ of the hybrid under study. The temperature and salt conditions can often be determined empirically in preliminary experiments in which samples of genomic DNA immobilized on filters are hybridized to the sequence of interest and then washed under conditions of different stringencies. See Sambrook, et al., supra, at page 9.50.

Variables to consider when performing, for example, a Southern blot are (1) the complexity of the DNA being blotted and (2) the homology between the target and the sequences being detected. The total amount of the polynucleotides to be studied can vary a magnitude of 10, from 0.1 to 1 μg for a plasmid or phage digest to $10^{-9}$ to $10^{-8}$ μg for a single copy gene in a highly complex eukaryotic genome. For lower complexity polynucleotides, substantially shorter blotting, hybridization, and exposure times, a smaller amount of starting polynucleotides, and lower specific activity of a target polynucleotide can be used. For example, a single-copy yeast gene can be detected with an exposure time of only 1 hour starting with 1 μg of yeast DNA, blotting for two hours, and hybridizing for 48 hours with a target polynucleotide radio labeled with $10^8$ cpm/μg. For a single-copy mammalian gene a conservative approach would start with 10 μg of DNA, blot overnight, and hybridize overnight in the presence of 10% dextran sulfate using a target polynucleotide radiolabeled with greater than $10^8$ cpm/μg, resulting in an exposure time of about 24 hours.

Several factors can affect the melting temperature ($T_m$) of a DNA-DNA hybrid between the target and sequence of interest, and consequently, the appropriate conditions for hybridization and washing. In many cases the target is not 100% homologous to the fragment. Other commonly encountered variables include the length and total G+C content of the hybridizing sequences and the ionic strength and formamide content of the hybridization buffer. The effects of all of these factors can be approximated by a single equation.

$T_m$=81+16.6(log 10 Ci)+0.4[% G+C)]−0.6(% formamide)−600/n−0.5(% mismatch), where Ci is the salt concentration (monovalent ions) and n is the length of the hybrid in base pairs (slightly modified from Meinkoth and Wahl, (1984) *Anal. Biochem.* 138:267 284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e., stringency), it becomes less likely for hybridization to occur between strands that are nonhomologous, and as a result, background decreases. If the labeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a target polynucleotide with 95% to 100% sequence identity to the sequence to be detected, 37° C. for 90% to 95% sequence identity, and 32° C. for 85% to 90% sequence identity. For lower percentage sequence identity, formamide content should be lowered and temperature adjusted accordingly, using the equation above. If the homology between the target polynucleotide and the sequence to be detected are not known, the simplest approach is to start with both hybridization and wash conditions which are nonstringent. If nonspecific bands or high background are observed after autoradiography, the filter can be washed at high stringency and reexposed. If the time required for exposure makes this approach impractical, several hybridization and/or washing stringencies should be tested in parallel. Stringent conditions include hybridization in a solution of at least about 5×SSC at 65° C., or at least about 4×SSC at 42° C.; see, for example, U.S. Pat. No. 5,707,829, the disclosure of which is herein incorporated by reference.

Generally, hybridization is performed using at least 18 contiguous nucleotides. That is, when at least 18 contiguous nucleotides are used as a probe, the probe will preferentially hybridize with a nucleic acid or mRNA comprising the complementary sequence, allowing the identification and retrieval of the nucleic acids of the biological material that uniquely hybridize to the selected probe. Probes of more than 18 nucleotides can be used, e.g. probes of from about 25 nucleotides to about 40 nucleotides, from about 50 nucleotides to about 72 nucleotides, up to the entire coding region can be used, but 18 nucleotides generally represents sufficient sequence for unique identification.

The nucleic acids may also include naturally occurring variants of the nucleotide sequences, e.g. degenerate variants, allelic variants, etc. Variants of the nucleic acids of the invention are identified by hybridization of putative variants with nucleotide sequences disclosed herein preferably by hybridization under stringent conditions. For example, by using appropriate wash conditions, variants of the nucleic acids can be identified where the allelic variant exhibits at most about 25-30% base pair mismatches relative to the selected nucleic acid probe. In general, allelic variants contain 15-25% base pair mismatches, and can contain as few as even 5-15%, or 2-5%, or 1-2% base pair mismatches, as well as a single base-pair mismatch.

Another embodiment provides homologs of GaTx2. Such homologs can be identified by any of a number of methods known to those skilled in the art. A fragment of the provided nucleic acid may be used as a hybridization probe against a cDNA library from the target organism of interest, where low stringency conditions are used. The probe may be a large fragment, or one or more short degenerate primers.

The homologs corresponding to the nucleic acids encoding SEQ ID NO: 1, where the source of homologous genes can be any related species within the same genus or group. Within a group, homologs have substantial sequence similarity, e.g. at least 75% sequence identity, usually at least 90%, more usually at least 95%, preferably 98% or greater between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared.

In some embodiments, the polynucleotide includes a nucleotide sequence encoding a polypeptide comprising at least about 5, 10, 15, 20, 25, 50, 75, 100, 125, or 150 amino acids of the sequence set forth in SEQ ID NO:1. In other embodiments, the polynucleotide includes a nucleotide sequence encoding the entire polypeptide having the amino acid sequence set forth in any one of SEQ ID NO: 1. In still other embodiments, the polynucleotide includes a nucleotide sequence which encodes a polypeptide comprising an amino acid sequence sharing at least about 60%, preferably at least about 70%, more preferably at least about 80%, even more preferably at least about 87%, 90%, 95%, 96%, 97%, 98%, or 99% or more amino acid sequence identity with the sequence depicted in SEQ ID NO:1.

As is known to one of skill in the art, using the standard genetic code table, a polynucleotide encoding a subject polypeptide can be designed and using a nucleic acid synthesizer or other means, a polynucleotide encoding a subject polypeptide may be produced.

Various derivatives of an antisense sequence specific for nucleic acids encoding GaTx2 may be prepared, where the phosphates may be modified, where oxygens may be substituted with sulfur and nitrogen, the sugars may be modified, and the like. The antisense sequences may be used by themselves or in conjunction with various toxic moieties, such as metal chelates, sensitizers, ribozymes, and the like. Antisense polynucleotides, and methods of using such, are described in numerous publications, including, e.g., *"Antisense Technology: A Practical Approach"* Lichtenstein and Nellen, eds. (1997) IRL Press.

Antisense molecules specific for GaTx2 can be used to down-regulate expression of GaTx2 in cells. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits its expression of the targeted gene products. Antisense molecules inhibit gene expression through various mechanisms, e.g. by, reducing the amount of mRNA available for translation, through activation of RNAse H, or steric hindrance. One or a combination of antisense molecules may be administered, where a combination may comprise two or more different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 75, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840 844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra.) Preferred oligonucleotides are chemically modified from the native phosphodiester structure, in order to increase their intracellular stability and binding affinity. Such modifications have been previously discussed with respect to the use of probes.

As an alternative to anti-sense inhibitors, catalytic nucleic acid compounds, e.g. ribozymes, anti-sense conjugates, siRNA, or microRNA etc. may be used to inhibit gene expression. Ribozymes may be synthesized in vitro and administered, or may be encoded on an expression vector, from which the ribozyme is synthesized in the targeted cell (for example, see International patent application WO 9523225, and Beigelman et al. (1995) *Nucl. Acids Res.* 23:4434 42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl. Biochem. Biotechnol.* 54:43 56.

One embodiment provides an siRNA specific for mRNA encoding GaTx2. Still another embodiment provides a microRNA specific for mRNA encoding GaTx2. Still another embodiment provides a vector encoding a siRNA or microRNA specific for GaTx2 mRNA. One of ordinary skill in the art could readily identify siRNAs using commercially available software.

Another embodiment provides GaTx2 genomic sequences. A genomic sequence of interest includes the nucleic acid present between the initiation codon and the stop codon, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, up to about 6 kb, of flanking genomic DNA at either the 5' or 3' end of the transcribed region. The genomic DNA may be isolated as a fragment of 50 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The sequence of the 5' flanking region may be utilized for promoter elements, including enhancer binding sites, that provide for regulation in tissues where scorpion toxins polypeptide are expressed. The tissue specific expression is useful for determining the pattern of expression, and for providing promoters that mimic the native pattern of expression. Naturally occurring polymorphisms in the promoter region are useful for determining natural variations in expression.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol. Med.* 1:194 205; Mortlock et al. (1996) *Genome Res.* 6:327 33; and Joulin and Richard-Foy (1995) *Eur. J. Biochem.* 232:620 626.

The regulatory sequences may be used to identify cis acting sequences required for transcriptional or translational regulation of expression, especially in different tissues or stages of development, and to identify cis acting sequences and trans-acting factors that regulate or mediate expression. Such transcription or translational control regions may be operably linked to one of the subject genes in order to promote expression of wild type or altered scorpion toxin polypeptide, or other proteins of interest in cultured cells.

The nucleic acid compositions may encode all or a part of GaTx2. Double or single stranded fragments of the DNA sequence may be obtained by chemically synthesizing oligonucleotides in accordance with conventional methods, by restriction enzyme digestion, by PCR amplification, etc. For the most part, DNA fragments will be of at least 15 nt, usually at least 25 nt or 35 nt or 45 nt but may be as long as 50 nt, 60 nt, 70 nt, 80 nt, and even as long as 90 nt or 100 nt. Small DNA fragments are useful as primers for PCR, hybridization screening probes, etc. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt, Algorithms for the selection of primer sequences are generally known, and are available in commercial software packages Amplification primers hybridize to complementary strands of DNA, and will prime towards each other.

The polynucleotides are isolated and obtained in substantial purity, generally as other than an intact chromosome. Usually, the DNA will be obtained substantially free of nucleic acid sequences other than a scorpion venom toxin-encoding polynucleotide, generally being at least about 50%, usually at least about 90% pure and are typically “recombinant”, i.e. flanked by one or more nucleotides with which it is not normally associated on a naturally occurring chromosome.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of scorpion toxin gene expression in the sample.

The sequence of a GaTx2-encoding nucleic acid or gene, including any flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one amino acid, and may differ by at least one or two but not more than about ten amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al., *Biotechniques* 14:22 (1993); Barany, *Gene* 37:111 23 (1985); Colicelli et al, *Mol. Gen. Genet.* 199:537 9 (1985); and Prentki et al., *Gene* 29:303 13 (1984). Methods for site specific mutagenesis can be found in Sambrook et al., *Molecular Cloning: A Laboratory Manual*, CSH Press 1989, pp. 15.3 15.108; Weiner et al., *Gene* 126:35 41 (1993); Sayers et al., *Biotechniques* 13:592 6 (1992); Jones and Winistorfer, *Biotechniques* 12:528 30 (1992); Barton et al., *Nucleic Acids Res.* 18:7349 55 (1990); Marotti and Tomich, *Gene Anal. Tech.* 6:67 70 (1989); and Zhu, *Anal. Biochem.* 177:120 4 (1989).

D. GaTx2 Homologs

Homologs and orthologs of scorpion toxin polypeptides, for example GaTx2, are identified by any of a number of methods. A fragment of scorpion venom toxin polynucleotide or cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Hybridization methods and conditions are well known in the art, see, e.g., U.S. Pat. No. 5,707,829. Nucleic acids having a region of substantial identity to a nucleic acid encoding GaTx2, e.g. allelic variants, genetically altered versions of the gene, etc., bind to the GaTx2 sequence under stringent hybridization conditions. By using probes, particularly labeled probes of DNA sequences, one can isolate homologous or related genes. The source of homologous genes can be any species of scorpion or any other organism that produces neurotoxins, e.g., snakes, arachnids, lizards, sea anemones, and the like. Between scorpion species, homologs have substantial sequence similarity, i.e. at least 75% sequence identity between nucleotide sequences, in some cases 80 or 90% sequence identity, and may be as high as 95%, 98%, or 99% sequence identity between closely related species. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J. Mol. Biol.* 215:403 10.

E. Pharmaceutical Compositions

Pharmaceutical compositions including a ClC channel ligand such as GaTx2 peptide are provided. Conditions alleviated or modulated by the administration of such compositions include those indicated below. Such pharmaceutical compositions may be for administration by oral, parenteral (intramuscular, intraperitoneal, intravenous (IV) or subcutaneous injection), transdermal (either passively or using iontophoresis or electroporation), transmucosal (nasal, vaginal, rectal, or sublingual) routes of administration or using bioerodible inserts and can be formulated in dosage forms appropriate for each route of administration. In general, pharmaceutical compositions are provided including effective amounts of a GaTx2 peptide, or derivative products, and pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., TWEEN 20, TWEEN 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., *Remington's Pharmaceutical Sciences*, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form.

1. Oral Delivery

GaTx2 peptide can be formulated for oral delivery. Oral solid dosage forms are described generally in *Remington's Pharmaceutical Sciences*, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by O, S. Banker and C. T. Rhodes Chapter 10, 1979, herein incorporated by reference. In general, the formulation will include the ClC channel ligands (or chemically modified forms thereof) and inert ingredients which allow for protection against the stomach environment, and release of the biologically active material in the intestine.

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

The peptides may be chemically modified so that oral delivery of the derivative is efficacious. Generally, the chemical modification contemplated is the attachment of at least one moiety to the component molecule itself where said moiety permits (a) inhibition of proteolysis; and (b) uptake into the blood stream from the stomach or intestine. Also desired is the increase in overall stability of the component or components and increase in circulation time in the body. As discussed above, PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowskli and Davis (1981) "Soluble Polymer-Enzyme Adducts," in *Enzymes as Drugs*. Hocenberg and Roberts, eds. (Wiley-Interscience. New York, N.Y.) pp. 367-383; and Newmark, et al. (1982) *J. Appl. Biochem.* 4:185-189].

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or derivative) or by release of the peptide (or derivative) beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used.

The peptide (or derivative) can be included in the formulation as fine multiparticulates in the form of granules or pellets of particle size about 1 mm. The formulation of the material for capsule administration could also be as a powder, lightly compressed plugs, or even as tablets. These therapeutics could be prepared by compression.

Colorants and/or flavoring agents may also be included. For example, the peptide (or derivative) may be formulated (such as by liposome or microsphere encapsulation) and then further contained within an edible product, such as a refrigerated beverage containing colorants and flavoring agents.

One may dilute or increase the volume of the peptide (or derivative) with an inert material. These diluents could include carbohydrates, especially mannitol, .alpha.-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-RX 1500, Emcompress and Avicell.

Disintegrants may be included in the formulation of the therapeutic into a solid dosage form. Materials used as disintegrants include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders and can include powdered gums such as agar, Karaya or tragacanth. Alginic acid and its sodium salt are also useful as disintegrants.

Binders may be used to hold the peptide (or derivative) agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation of the peptide (or derivative) to prevent sticking during the formulation process. Lubricants may be used as a layer between the peptide (or derivative) and the die wall, and these can include but are not limited to: stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the peptide (or derivative) into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the peptide (or derivative) are for instance the fatty acids oleic acid, linoleic acid and linolenic acid.

Controlled release oral formulations may be desirable. The peptide (or derivative) could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The peptide (or derivative) could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

2. Parenteral Delivery

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

3. Rectal or Vaginal Delivery

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

4. Pulmonary Delivery

Also contemplated herein is pulmonary delivery of the GaTx2 peptides (or derivatives thereof). The peptide (or derivative) is delivered to the lungs of a mammal while inhaling and traverses across the lung epithelial lining to the blood stream [see, e.g., Adjei, et al. (1990) *Pharmaceutical Research* 7:565-569; Adjei, et al. (1990) *Int. J. Pharmaceutics* 63:135-144 (leuprolide acetate); Braquet, et al. (1989) *J. Cardiovascular Pharmacology* 13(sup5):143-146 (endothelin-1); Hubbard, et al. (1989) Annals of Internal Medicine, Vol. III, pp. 206-212 (α1-antitrypsin); Smith, et al. (1989) *J. Clin. Invest* 84:1145-1146 (.alpha.-1-proteinase); Oswein, et al. (1990) “Aerosolization of Proteins”, *Proceedings of Symposium on Respiratory Drug Delivery II* Keystone, Colorado (recombinant human growth hormone); Debs, et al. (1988) *J. Immunol* 140:3482-3488 (interferon-.gamma. and tumor necrosis factor .alpha.); and U.S. Pat. No. 5,284,656 to Platz, et al. (granulocyte colony stimulating factor). A method and composition for pulmonary delivery of drugs for systemic effect is described in U.S. Pat. No. 5,451,569 to Wong, et al.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc, Research Triangle Park, N.C.); and the Spinhaler powder inhaler (Fisons Corp., Bedford, Mass.).

All such devices require the use of formulations suitable for the dispensing of peptide (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified peptides may also be prepared in different formulations depending on the type of chemical modification or the type of device employed.

Formulations suitable for use with a nebulizer, either jet or ultrasonic, will typically comprise peptide (or derivative) dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the peptide (or derivative) caused by atomization of the solution in forming the aerosol.

Formulations for use with a metered-dose inhaler device will generally include a finely divided powder containing the peptide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof, Suitable surfactants include sorbitan trioleate and soya lecithin. Oleic acid may also be useful as a surfactant.

Formulations for dispensing from a powder inhaler device will include a finely divided dry powder containing peptide (or derivative) and may also include a bulking agent, such as lactose, sorbitol, sucrose, or mannitol in amounts which facilitate dispersal of the powder from the device, e.g., 50 to 90% by weight of the formulation. The peptide (or derivative) should most advantageously be prepared in particulate form with an average particle size of less than 10 mm (or microns), most preferably 0.5 to 5 mm, for most effective delivery to the distal lung.

5. Nasal Delivery

Nasal delivery of the ClC channel ligand (or derivatives) is also contemplated. Nasal delivery allows the passage of the peptide to the blood stream directly after administering the therapeutic product to the nose, without the necessity for deposition of the product in the lung. Formulations for nasal delivery include those with dextran or cyclodextran.

Other penetration-enhancers used to facilitate nasal delivery are also contemplated for use with the peptides of the present invention (such as described in International Patent Publication No. WO 2004056314, filed Dec. 17, 2003, incorporated herein by reference in its entirety).

6. Dosages

For all of the peptide compounds, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower. The pharmaceutical compositions are formulated to contain an amount of GaTx2 effective to inhibit ClC channels when administered to a host in need thereof.

7. Polymeric Matrices

Both non-biodegradable and biodegradable matrices can be used for delivery of ClC channel ligands such as GaTx2 peptides, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

Representative synthetic polymers that cal be used for delivery include polyamides, polycarbonates, polyalkylenes, polyallylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxyethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof. Examples of biodegradable polymers include synthetic polymers such as polymers of lactic acid and glycolic acid, polyanhydrides, poly(ortho) esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof, In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in *Macromolecules,* 1993, 26, 581-587, polyhyaluronic acids, casein, gelatin, glutin, polyanhydrides, polyacrylic acid, alginate, chitosan, poly(methyl methacrylates), poly(ethylmethacrylates), poly(butylmethaerylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

The matrices can be formed by solvent evaporation, spray drying, solvent extraction and other methods known to those skilled in the art.

Bioerodible microspheres can be prepared using any of the methods developed for making microspheres for drug delivery, for example, as described by Mathiowitz and Langer, *J. Controlled Release* 5, 13-22 (1987); Mathiowitz, et al., *Reactive Polymers* 6, 275-283 (1987); and Mathiowitz, et al., *J. Appl. Polymer Sci.* 35, 755-774 (1988). The selection of the method depends on the polymer selection, the size, external morphology, and crystallinity that is desired, as described, for example, by Mathiowitz, et al., *Scanning Microscopy* 4,329-340 (1990); Mathiowitz, et al., *J. Appl. Polymer Sci.* 45, 125-134 (1992); and Benita, et al., *J. Pharm. Sci.* 73, 1721-1724 (1984). In solvent evaporation, described for example, in Mathiowitz, et al., (1990), Benita, and U.S. Pat. No. 4,272, 398 to Jaffe, the polymer is dissolved in a volatile organic solvent. The peptide either in soluble form or dispersed as fine particles, is added to the polymer solution, and the mixture is suspended in an aqueous phase that contains a surface active agent such as poly(vinyl alcohol). The resulting emulsion is stirred until most of the organic solvent evaporates, leaving solid microspheres. In general, the polymer can be dissolved in methylene chloride. Microspheres with different sizes (1-1000 microns) and morphologies can be obtained by this method which is useful for relatively stable polymers such as polyesters and polystyrene. However, labile polymers such as polyanhydrides may degrade due to exposure to water. For these polymers, hot melt encapsulation and solvent removal may be preferred.

In hot melt encapsulation, the polymer is first melted and then mixed with the solid particles of peptides. The mixture is suspended in a non-miscible solvent such as silicon oil and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with diameters between one and 1000 microns can be obtained with this method. The external surface of spheres prepared with this technique is usually smooth and dense. This procedure is useful with water labile polymers, but is limited to use with polymers with molecular weights between 1000 and 50000. Solvent removal was primarily designed for use with polyanhydrides. In this method, the drug is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike solvent evaporation, this method can be used to make microspheres from polymers with high melting points and a wide range of molecular weights. Microspheres having a diameter between one and 300 microns can be obtained with this procedure. The external morphology of the spheres is highly dependent on the type of polymer used. In spray drying, the polymer is dissolved in methylene chloride (0.04 g/ml). A known amount of active drug is suspended (if insoluble) or co-dissolved (if soluble) in the polymer solution. The solution or the dispersion is then spray-dried. Double walled microspheres can be prepared according to U.S. Pat. No. 4,861,627 to Mathiowitz.

Hydrogel microspheres made of gel-type polymers such as alginate or polyphosphazines or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as described, for example, by Salib, et al., Pharmazeutische Industrie 40-11A, 1230 (1978). Chitosan microspheres can be prepared by dissolving the polymer in acidic solution and crosslinking with tripolyphosphate. For example, carboxymethylcellulose (CMC) microsphere are prepared by dissolving the polymer in an acid solution and precipitating the microspheres with lead ions. Alginate/polyethylene imide (PEI) can be prepared to reduce the amount of carboxyl groups on the alginate microcapsules.

Other delivery systems including films, coatings, pellets, slabs, and devices can be fabricated using solvent or melt casting, and extrusion, as well as standard methods for making composites. The polymer can be produced by first mixing monomers and peptides as described by Sawhney, et al., and polymerizing the monomers with UV light. The polymerization can be carried out in vitro as well as in vivo.

F. Fusion Proteins

Another embodiment provides a fusion protein including GaTx2 or a biologically active fragment thereof is fused to a heterologous peptide or protein. A fusion protein is a protein created through genetic engineering from two or more proteins/peptides. This is achieved by creating a fusion gene: removing the stop codon from the DNA sequence of the first protein, then appending the DNA sequence of the second protein in frame. That DNA sequence will then be expressed by a cell as a single protein.

In one embodiment a linker (or "spacer") peptides are also added which make it more likely that the proteins fold independently and behave as expected. Especially in the case where the linkers enable protein purification, linkers in protein or peptide fusions can be engineered with cleavage sites for proteases or chemical agents which enable the liberation of the two separate proteins.

The disclosed fusion proteins are useful for identification and purification of GaTx2, by fusing a GST protein, FLAG peptide, or a hexa-his peptide (a 6xhis-tag) which can be isolated using nickel or cobalt resins (affinity chromatography).

In one embodiment GaTx2 or derivative thereof can be fused to a cytotoxic moiety such as ricin, saporin, or pseudonomas exotoxin. Such fusion proteins can be useful for delivering cytotoxic materials to cells with chloride channels.

In another embodiment, GaTx2 peptide can be labeled with a radioisotope, for example $I^{125}$, fluorophore, or other detectable agent. Labeled GaTx2 can be useful for detecting chloride channels in a biological sample, in particular for detecting ClC-2, or for the selective ablation of cells over-producing ClC-2.

Still another embodiment provides an ClC channel ligand fused to protein transduction domain, localization signal or both. Protein transduction domains include but are not limited to HIV TAT YGRKKRRQRRR (SEQ. ID NO. 2) or RKKRRQRRR (SEQ. ID NO. 3); 11 Arginine residues, or positively charged polypeptides or polynucleotides having 8-15 residues, preferably 9-11 residues, Antp SGRQIKIWFQN-RRMKWKKC (SEQ ID NO:4), and HIV Tat SGYGRKKRRQRRRC (SEQ ID NO:5).

The ClC channel ligand can be operably linked to an antibody or antigen-binding fragment of the antibody so that the ClC channel ligand can be selectively delivered to a target expressing an epitope recognized by the antibody. The antibody can be a single chain antibody, monoclonal antibody, polyclonal antibody, humanized antibody, or chimeric antibody.

III. Methods of Manufacture

A. Purification

A bioassay-guided fractionation of Lqh venom may be used to isolate a peptide ligand that interacts with ClC channels, for example ClC-2. The fractionation approach may include, for example, the following steps: homogenization to disrupt mucus contained in the venom, recovery of components below 10 kDa molecular weight by separation through a centrifuge filter resulting in "Lqh-pf venom", testing for activity against the ion channel expressed in *Xenopus oocytes*, using recordings from inside-out or outside-out single-channel patches or macropatches, fractionation according to hydrophobicity by reversed-phase HPLC(RP-HPLC) in a gradient of acetonitrile in water, testing fractions for activity against ClC-2 expressed in *Xenopus oocytes*, using recordings from inside-out or outside-out single-channel patches or macropatches or TEVC, desalting of fractions using RP-HPLC, with collection of individual chromatographic peaks, testing for activity against the ion channel expressed in *Xenopus oocytes*, using recordings from single-channel patches and/or macropatches, characterization of material represented in individual chromatographic peak using MALDI-TOF, and breaking of the disulfide bridges in the isolated toxin by reduction and subsequent carboxamidomethylation of free cysteines. The primary sequence may be determined using Edman degradation, but any known method of amino acid sequences may be used.

B. Synthesis of ClC Channel Ligands

Certain embodiments provide peptides that selectively bind to ClC channels including anion channels and inhibit the transport anions through the channel. These peptide ligands of anion channels can be synthesized using general methods for peptide synthesis and purification, and disulfide bond formation, known in the art. As described in the Examples, linear peptides were produced by solid phase synthesis using 9-fluorenylmethoxycarbonyl (Fmoc) chemistry. Coupling of Fmoc amino acids was performed using the HBTU/HOBT/DIPEA method on an Applied Biosystems 431A synthesizer. The purified linear peptide was subjected to oxidative cyclization under equilibrating conditions in order to promote formation of the most stable disulfide bridges, with the reaction being monitored by analytical HPLC. Cyclized peptide was isolated from the acidified reaction mixture by reversed phase extraction, was purified by HPLC, and was characterized by MALDI-MS for molecular weight determination and by analytical HPLC for comparison with the native toxin.

Another embodiment provides polypeptides having 97%, 98% or 99% sequence identity or greater to SEQ ID NO: 1, preferably having 99% sequence identity or greater to SEQ ID NO: 1 optionally where one or more amino acids are modified, such as by incorporation of biotin, or are substituted by non-natural amino acids.

Synthetic peptides representing portions of the instant amino acid sequences may be synthesized by solid-phase chemistry. Alternatively, toxin peptides may be produced by recombinant methods upon expression in prokaryotic or eukaryotic cells, These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

IV. Methods of Using ClC Channel Ligands

A. Methods of Treatment

Diseases, disorders, or symptoms of disease or disorders related to aberrant ClC channel activity can be treated using the disclosed ClC channel ligands. For example, diseases associated with defective or overactive ion channels, in particular chloride channels, can be treated using the disclosed peptides and peptide compositions. One embodiment provides a method of treating a subject by administering to the subject an effective amount of the pharmaceutical composition including a therapeutically effective amount of a ClC channel ligand, for example GaTx2, a variant or a pharmaceutically acceptable salt or solvate thereof. By "pharmaceutically acceptable salts" is meant any salts that are known or later discovered to be pharmaceutically acceptable. Some examples are: acetate; trifluoroacetate; hydrohalides, such as hydrochloride and hydrobromide; sulfate; citrate; maleate; tartrate; glycolate; gluconate; succinate; mesylate; besylate; and oxalate salts. Some diseases attributed to defective, aberrant or overactive ion channels, in particular overactive chloride ion channels include cancer, cystic fibrosis, epilepsy, renal tubular disorders, Bartter's syndrome, Dent's disease, myotonia, osteopetrosis, Angleman or Prader-Willi, upregulation of chloride channels in glioma cells, diarrhea-predominant inflammatory bowel syndrome, secretory diarrhea, excitotoxic neuronal injury, and in autosomal dominant polycystic kidney disease (ADPKD).

Another embodiment provides a method of treating a disorder or a symptom of disorder selected from the group consisting of cancer, cystic fibrosis, epilepsy, renal tubular disorders, Bartter's syndrome, Dent's disease, myotonia, osteopetrosis, Angleman or Prader-Willi, upregulation of chloride channels in glioma cells, diarrhea-predominant inflammatory bowel syndrome, autosomal dominant polycystic kidney disease (ADPKD), excitotoxic neuronal injury, and secretory diarrhea, as well as other disorders, by administering to a host in need thereof an effective amount of GaTx2, a variant, derivative, or a prodrug thereof.

Yet another embodiment provides a method for reducing ClC channel activity by contacting the ClC channel with a ligand having at least 97% sequence identity to SEQ ID NO: 1.

Another embodiment provides a method for reducing chloride channel function by contacting the chloride channel with a GaTx2 peptide, variant, derivative or prodrug thereof.

Still another embodiment provides a method for treating a disorder or symptom of a disorder related to an overactive chloride channel including administering a pharmaceutical composition including an effective amount of GaTx2, a derivative, variant or prodrug thereof.

Another embodiment provides a method for reducing chloride ion transport through ClC-2 by contacting ClC-2 with a peptide ligand or biologically active fragment thereof isolated from scorpion venom. The scorpion venom peptide ligand can be GaTx2 or a biologically active fragment thereof.

Another embodiment provides a method of inhibiting an ClC channel or a domain thereof by contacting the ClC channel with GaTx2, a variant thereof, a derivative thereof, or a biologically active fragment thereof.

In one embodiment the GaTx2 is a ligand for one or more ClC channels.

B. Detection Methods

Various embodiments provide a variety of detection methods, which methods are useful in diagnostic assays. Also provided are a variety of screening assays, which assays are useful for identifying agents which affect ClC channel ligand activity (e.g., ion channel binding) and/or ClC channel ligand mRNA and/or polypeptide levels. Detection methods include methods for detecting ClC channel ligands in a biological sample, methods for detecting ClC channel ligand mRNA in a biological sample, and methods for detecting ClC channel ligand-ion channel binding in a biological sample.

1. Methods of Detecting GaTx2 in a Biological Sample

Other embodiments provide methods for detecting the presence and/or measuring a level of an ClC channel ligand, for example GaTx2, in a biological sample, using a ClC channel ligand-specific antibody. The methods generally include:

a) contacting the sample with an antibody specific for GaTx2; and b) detecting binding between the antibody and molecules of the sample.

Detection of specific binding of the GaTx2-specific antibody, when compared to a suitable control, is an indication that ClC channel ligands are present in the sample. Suitable controls include a sample known not to contain a ClC channel ligand (GaTx2); and a sample contacted with an antibody not specific for a ClC channel ligand, e.g., an anti-idiotype antibody. A variety of methods to detect specific antibody-antigen interactions are known in the art and can be used in the method, including, but not limited to, standard immunohistological methods, immunoprecipitation, an enzyme immunoassay, and a radioimmunoassay. In general, the scorpion venom toxin polypeptide-specific antibody will be delectably labeled, either directly or indirectly. Direct labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. The antibody may be attached (coupled) to an insoluble support, such as a polystyrene plate or a bead. Indirect labels include second antibodies specific for scorpion venom toxin polypeptide-specific antibodies, wherein the second antibody is labeled as described above; and members of specific binding pairs, e.g., biotin-avidin, and the like. The biological sample may be brought into contact with and immobilized on a solid support or carrier, such as nitrocellulose, that is capable of immobilizing cells, cell particles, or soluble proteins. The support may then be washed with suitable buffers, followed by contacting with a detectably-labeled scorpion venom toxin polypeptide-specific antibody. Detection methods are known in the art and will be chosen as appropriate to the signal emitted by the detectable label. Detection is generally accomplished in comparison to suitable controls, and to appropriate standards.

Still other embodiments provide methods for detecting the presence and/or measuring a level of GaTx2 in a biological sample. The methods generally comprise:

a) contacting the sample with an ClC channel, for example ClC-2 protein or fragment thereof, and b) detecting binding between the ClC channel and molecules of the sample.

Detection of specific binding of the ClC channel is an indication that GaTx2 polypeptides are present in the sample.

Methods for detecting binding between a ClC channel ligand and an ClC channel are known in the art and include immunoprecipitation of ClC channel-ligand complexes using an antibody specific to the ClC channel ligand or ClC channel, as long as the antibody does not disrupt ClC channel ligand-ClC channel binding. Alternatively, the ion channel polypeptide used may be a fusion protein which provides for specific immunoprecipitation of the fusion partner, an enzymatic detection, a fluorescent signal (e.g., a green fluorescent protein). The ion channel polypeptide can be labeled with any detectable label, as described below. The ion channel polypeptide can be attached, directly or through a linker, to an insoluble support (e.g., polystyrene beads, magnetic beads, and the like), thereby providing a means for separating scorpion toxin family polypeptide-ion channel/receptor complexes from the biological sample, and subsequently detecting the presence of and/or measuring the amount (level) of scorpion venom toxin polypeptide. The latter method can also be used to identify new proteins that bind to GaTx2, such as other ion channels/receptors.

Binding of ClC channel ligand to the ion channel may also be detected by monitoring ion channel activity, using methods such as electrophysiology (two electrode voltage clamp or single electrode patch clamp), guanidinium ion flux assays, toxin-binding assays, and Fluorometric Imaging Plate Reader (FLIPR) assays. (See, e.g., Sullivan, et al. (1999) *Methods Mol. Biol.* 114:125 133; Siegel and Isacoff (1997) *Neuron* 19:1 20; and Lopatin, et al. (1998) *Trends Pharmacol. Sci.* 19:395 398.)

2. Methods of Detecting GaTx2 mRNA in a Biological Sample

One embodiment provides methods for detecting the presence of ClC channel ligand mRNA in a biological sample. The methods can be used, for example, to assess whether a test compound affects ClC channel ligand gene expression, directly or indirectly.

An exemplary method generally includes:
 a) contacting the sample with a ClC channel ligand-encoding polynucleotide under conditions which allow hybridization; and
 b) detecting hybridization, if any.

Detection of hybridization, when compared to a suitable control, is an indication of the presence in the sample of a ClC channel ligand-encoding polynucleotide, for example a GCaTx2-encoding polynucleotide. Appropriate controls include, for example, a sample which is known not to contain ClC channel ligand-encoding polypeptide mRNA, and use of a labeled polynucleotide of the same "sense" as a ClC channel ligand mRNA. Conditions which allow hybridization are known in the art, and have been described in more detail above. Detection can be accomplished by any known method, including, but not limited to, in situ hybridization, PCR, RT-PCR, and "Northern" or RNA blotting, or combinations of such techniques, using a suitably labeled ClC channel ligand polynucleotide. A variety of labels and labeling methods for polynucleotides are known in the art and can be used in the assay methods of the invention. Specific hybridization can be determined by comparison to appropriate controls.

Methods using PCR amplification can be performed on the DNA from a single cell, although it is convenient to use at least about $10^5$ cells. The use of the polymerase chain reaction is described in Saiki et al. (1985) *Science* 239:487, and a review of current techniques may be found in Sambrook, et al. *Molecular Cloning: A Laboratory Manual*, CSH Press 1989, pp. 14.2314.33. A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4=,5=-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N=,N-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

C. Research Tools

The disclosed peptide ClC channel ligands can be used to investigate ClC channel structure and function. For example, GaTx2 can be used as a structural probe of the ClC-2 or its domains, or any other member of the ClC channel superfamily, or their domains. For example, GaTx2, or a derivative of GaTx2, can be used to stabilize the conformation of ClC-2 protein, or its domains, or any other member of the ClC channel superfamily, or their domains, in crystallization experiments.

Additionally, GaTx2, or a derivative of GaTx2, can be used to isolate ClC-2, or its domains, or any other member of the ClC channel superfamily, or their domains, by way of affinity chromatography wherein GaTx2, or a derivative of GaTx2, is coupled to a solid support.

One embodiment provides a method for isolating ClC-2 protein by attaching a peptide having at least 97% sequence identity to SEQ ID NO: 1 to a solid support and contacting the peptide on the solid support with a sample containing ClC2 under conditions promoting the interaction of the peptide with ClC-2 to retain ClC-2. Conditions that promote interaction between the peptide and ClC-2 include physiological conditions of pH, salt concentration, and temperature. The solid support can be washed with neutral buffer to remove non-specifically bound components. Next, ClC-2 is eluted from the solid support for example by increasing the salt concentration in the elution buffer.

V. Screening Assays

Another embodiment provides screening methods for identifying agents which modulates ClC channel ligand-ClC channel binding activity such as GaTx2-ClC channel binding activity, methods for identifying agents which modulate GaTx2-ClC channel interaction, methods for identifying agents which modulate a level of GaTx2 in a cell, and methods for identifying agents which modulate a level of GaTx2 mRNA in a cell.

As used herein, the term "modulate" encompasses "increase" and "decrease". Of particular interest are agents which modulate GaTx2-ClC channel binding activity, and/or which modulate GaTx2-ion channel interaction, and/or which modulate a level of ClC channel ligand in a cell, and/or which modulate a level of GaTx2 mRNA in a cell. Such agents are of interest as candidates for treating diseases or disorders associated with ion channels, including, but not limited to those associated with chloride channels (e.g., excitotoxic neuronal injury, epilepsy, renal tubular disorders, Bartter's syndrome, cystic fibrosis, osteopetrosis, Angleman or Prader-Willi, upregulation of chloride channels in glioma cells, etc.), sodium channels (e.g., Hyperkalemic periodic paralysis, hypokalemic periodic paralysis, congenital Paramyotonia, Myotonia Fluctuans, Myotonia Permanens, Acetazolamide-responsive myotonia, malignant hyperthermia, nerve injury, epilepsy, various heart diseases, thyroid, endocrine, etc.).

The terms "agent", "substance" and "compound" are used interchangeably herein. Candidate agents encompass numerous chemical classes, typically synthetic, semi-synthetic, or naturally-occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and typically include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Furthermore, pharmacophores may be designed based on the structural aspects of the ion channel/receptor binding interfaces of scorpion venom toxin polypeptides.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components can be added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

1. Methods for Identifying Agents that Modulate GaTx2-Ion Channel Binding Activity One embodiment provides methods of identifying agents which modulate ClC channel binding activity of ClC channel ligands. The term "modulate" encompasses an increase or a decrease in the measured ClC channel ligand-ClC channel binding activity when compared to a suitable control.

The method generally comprises:

a) contacting a substance to be tested with a sample containing a ClC channel ligand such as GaTx2 and a chloride ion channel such as a ClC channel; and b) measuring ClC channel binding activity of the ClC channel ligand in the presence of the substance.

An increase or a decrease in ClC channel binding activity in comparison to ClC channel binding activity in a suitable control (e.g., a sample including ClC channel ligand and an ClC channel in the absence of the substance being tested) is an indication that the substance modulates a ClC channel binding activity of the ClC channel ligand.

Methods for practicing such assays are known to those of skill in the art. (See, e.g., Mishina et al. (1985) *Nature* 313: 364 369; and Noda, et al. *Nature* 322:836 828.) For example, ion channel activity may be measured by methods such as electrophysiology (two electrode voltage clamp or single electrode patch clamp), guanidinium ion flux assays, toxin-binding assays, and Fluorometric Imaging Plate Reader (FLIPR) assays. (See, e.g., Sullivan, et al. (1999) *Methods Mol. Biol.* 114:125 133; Siegel and Isacoff (1997) *Neuron* 19:1 20; and Lopatin, et al. (1998) *Trends Pharmacol. Sci.* 19:395 398.)

An "agent which modulates ClC channel-ClC channel ligand binding activity", as used herein, describes any molecule, e.g. synthetic or natural organic or inorganic compound, protein or pharmaceutical, with the capability of altering ClC channel binding activity of a ClC channel ligand, as described herein. Generally a plurality of assay mixtures are run in parallel with different agent concentrations to obtain a differential response to the various concentrations. Typically, one of these concentrations serves as a negative control, i.e. at zero concentration or below the level of detection. Ion channel binding can be measured as described hereinabove.

An agent which modulates ClC channel binding activity of a ClC channel ligand increases or decreases the activity at least about 10%, at least about 15%, at least about 20%, at least about 25%, more preferably at least about 50%, more preferably at least about 100%, or 2-fold, more preferably at least about 5-fold, more preferably at least about 10-fold or more when compared to a suitable control.

2. Methods of Detecting Agents which Modulate a Level of GaTx2 mRNA and/or Polypeptide A wide variety of cell-based assays may be used for identifying agents which modulate levels of ClC channel ligand polypeptide mRNA, using, for example, a mammalian cell transformed with a construct including a ClC channel-encoding cDNA such that the cDNA is overexpressed, or, alternatively, a construct including a ClC channel gene promoter operably linked to a reporter gene.

Accordingly, one embodiment provides a method for identifying an agent, particularly a biologically active agent, that modulates a level of ClC channel ligand expression in a cell, the method including: combining a candidate agent to be tested with a cell comprising a nucleic acid which encodes a ClC channel ligand; and determining the effect of said agent on ClC channel ligand expression. A modulation of ClC channel ligand expression levels includes increasing the level and decreasing the level of ClC channel ligand mRNA and/or scorpion venom toxin encoded by the scorpion venom toxin polynucleotide when compared to a control lacking the agent being tested. An increase or decrease of about 1.25-fold, usually at least about 1.5-fold, usually at least about 2-fold, usually at least about 5-fold, usually at least about 10-fold or more, in the level (i.e., an amount) of ClC channel ligand mRNA and/or polypeptide following contacting the cell with a candidate agent being tested, compared to a control to which no agent is added, is an indication that the agent modulates ClC channel ligand expression.

An agent being tested for its effect on ClC channel ligand expression is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit cytotoxic activity are considered candidate agents.

The cells used in the assay are usually mammalian cells, including, but not limited to, rodent cells and human cells. The cells may be primary cell cultures.

Scorpion venom toxin family polypeptide mRNA and/or polypeptide whose levels are being measured can be encoded by an endogenous scorpion venom toxin polynucleotide, or the scorpion venom toxin polynucleotide can be one that is comprised within a recombinant vector and introduced into the cell, i.e., the ClC channel ligand mRNA and/or polypeptide can be encoded by an exogenous scorpion venom toxin polynucleotide. For example, a recombinant vector may comprise an isolated ClC channel ligand transcriptional regulatory sequence, such as a promoter sequence, operably linked to a reporter gene (e.g., β-galactosidase, CAT, luciferase, or other gene that can be easily assayed for expression). In these embodiments, the method for identifying an agent that modulates a level of ClC channel ligand expression in a cell, comprises: combining a candidate agent to be tested with a cell comprising a nucleic acid which comprises a scorpion venom toxin gene transcriptional regulatory element operably linked to a reporter gene; and determining the effect of said agent on reporter gene expression. A recombinant vector may comprise an isolated ClC channel ligand transcriptional regulatory sequence, such as a promoter sequence, operably linked to sequences coding for a ClC channel ligand; or the transcriptional control sequences can be operably linked to coding sequences for a scorpion venom toxin fusion protein comprising ClC channel ligand fused to a polypeptide which facilitates detection. In these embodiments, the method comprises combining a candidate agent to be tested with a cell comprising a nucleic acid which comprises a scorpion venom toxin gene transcriptional regulatory element operably linked to a ClC channel ligand-coding sequence; and determining the effect of said agent on ClC channel ligand expression, which determination can be carried out by measuring an amount of ClC channel ligand mRNA, ClC channel ligand, or scorpion venom toxin fusion polypeptide produced by the cell.

Cell-based assays generally comprise the steps of contacting the cell with an agent to be tested, forming a test sample, and, after a suitable time, assessing the effect of the agent on ClC channel ligand expression. A control sample comprises the same cell without the candidate agent added. ClC channel ligand expression levels are measured in both the test sample and the control sample. A comparison is made between ClC channel ligand expression level in the test sample and the control sample. ClC channel ligand expression can be assessed using conventional assays. For example, when a mammalian cell line is transformed with a construct that results in expression of ClC channel ligand, ClC channel ligand mRNA levels can be detected and measured, as described above, or ClC channel ligand levels can be detected and measured, as described above. A suitable period of time for contacting the agent with the cell can be determined empirically, and is generally a time sufficient to allow entry of the agent into the cell and to allow the agent to have a measurable effect on ClC channel ligand mRNA and/or polypeptide levels. Generally, a suitable time is between 10 minutes and 24 hours, more typically about 18 hours. Methods of measuring ClC channel ligand mRNA levels are known in the art, several of which have been described above, and any of these methods can be used in the methods of the present invention to identify an agent which modulates ClC channel ligand mRNA level in a cell, including, but not limited to, a PCR, such as a PCR employing detectably labeled oligonucleotide primers, and any of a variety of hybridization assays. Similarly, ClC channel ligand levels can be measured using any standard method, several of which have been described herein, including, but not limited to, an immunoassay such as ELISA, for example an ELISA employing a detectably labeled antibody specific for a ClC channel ligand.

VI. Preparation of Antivenom and Antibodies

Identification of potent components is an important first step in designing and obtaining effective antivenom. Antibodies raised against the critical toxic components have the potential to block the toxic effects and reduce the pain associated with the scorpion envenomation. Antibodies that specifically bind to scorpion venom toxin polypeptides, in particular to GaTx2 are produced by: 1) immunization of non-human animals with the isolated proteins and production of hybridomas; and 2) identification of antibodies that specifically bind scorpion venom toxin polypeptides (e.g., by screening hybridoma supernatants with scorpion venom toxin). Each of these steps is described below.

Antibodies specific to GaTx2 are produced by immunizing a non-human mammal (e.g., murine, rodentia, lagomorpha, ovine, porcine, bovine, etc.) with isolated GaTx2. Immunization and hybridoma production with the scorpion venom toxin polypeptide can be accomplished according to conventional methods well known in the art. The immunized animal is an immunocompetent, non-human mammalian host, including murine, rodentia, lagomorpha, ovine, porcine, bovine, etc., which is immunized with scorpion venom toxin polypeptide isolated as described above. The choice of a particular host is primarily one of convenience. Immunizations are generally performed in accordance with conventional techniques.

Either monoclonal or polyclonal antibodies, preferably monoclonal antibodies (MAbs), are produced from the immunized animal. Polyclonal antisera may be harvested from serum in accordance with conventional methods after completion of the immunization schedule. For production of MAbs, lymphocytes are harvested from the appropriate lymphoid tissue, e.g. spleen, draining lymph node, etc., and fused with an appropriate fusion partner, usually a myeloma line, producing a hybridoma secreting a specific monoclonal antibody. Methods for hybridoma production are well known in the art (see, e.g., *Antibodies, A Laboratory Manual*, Harlow & Lane eds., (1988) Cold Spring Harbor Press).

The antibodies and MAbs can be modified in any of a variety of ways, with the proviso that the modified MAbs retain substantially specific binding to the original antigen (e.g., to the original scorpion venom toxin polypeptide). The ability of such modified antibodies to specifically and sensitively bind their original antigen can be assessed in in vitro assays as described herein (e.g., to assess binding of the modified antibodies to scorpion venom toxin in cytospin preparations, to scorpion venom toxin cell-specific polypeptides in ELISA assays, etc.). Such screening is routine and, with the guidance provided herein, within the skill of the ordinarily skilled artisan.

Modified antibodies contemplated by the present invention include those produced using biochemical, chemical, or recombinant DNA techniques. For example, antibody fragments, such as Fv, F(ab')2 and Fab may be prepared from the antibodies of the invention by cleavage of the intact protein, e.g., by protease or chemical cleavage. Alternatively, a truncated gene is designed. For example, a chimeric gene encoding a portion of the F(ab')2 fragment would include DNA sequences encoding the CH1 domain and hinge region of the H chain, followed by a translational stop codon to yield the truncated molecule. Preferably, such antibody fragments retain antigen avidity and/or affinity that is substantially the same as the original antibody from which they are derived.

The subject antibodies may also be produced as a single chain, instead of the normal multimeric structure. Single chain antibodies are described in Jost et al. (1994) *J. Biol. Chem.* 269:26267 73, and others. DNA sequences encoding the variable region of the heavy chain and the variable region of the light chain are ligated to a spacer encoding at least about four amino acids of small neutral amino acids, including glycine and/or serine. The protein encoded by this fusion allows assembly of a functional variable region that retains the specificity and affinity of the original antibody.

The antibodies may also be humanized. Methods of humanizing antibodies are well known in the art. The humanized antibody may be the product of an animal having transgenic human immunoglobulin (Ig) constant region genes (see for example, WO 90/10077 and WO 90/04036). Alternatively, the antibody of interest may be engineered by recombinant DNA techniques to substitute the $CH_1$, $CH_2$, $CH_3$, hinge domains, and/or the framework residues with the corresponding human sequence (see WO 92/02190). Humanized antibodies are of particular interest for in vivo use in humans.

The antibodies may also be used to produce chimeric antibodies. The use of Ig cDNA for construction of chimeric Ig genes is known in the art (Liu et al. (1987) *Proc. Natl. Acad. Sci.* 84:3439; Liu et al. (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91 3242. Human C region genes are readily available from known clones. The chimeric, humanized antibody is then expressed by conventional methods.

Expression vectors for use in modification of the antibodies of the invention are well known in the art and include plasmids, retroviruses, YACs, EBV derived episomes, and the like, For example, where the scorpion venom toxin polypeptide antibody is to be modified to provide a human antibody heavy and/or light chain constant region, a convenient vector is one that encodes a functionally complete human CH or CL Ig sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Biol*, 3:280), Rous sarcoma virus LTR (Gorman et al. (1982) *Proc. Natl. Acad. Sci.* 79:6777), and Moloney murine leukemia virus LTR (Grosschedl et al. (1985) *Cell* 41:885); native Ig promoters, etc.

VII. Kits

The detection methods discussed above can be provided as part of a kit. Thus, one embodiment provides kits for detecting the presence and/or a level of ClC channel ligand or ClC channel ligand-encoding polynucleotides in a biological sample. Procedures using these kits can be performed by clinical laboratories, experimental laboratories, medical practitioners, or private individuals. The kits for detecting a ClC channel ligand include a moiety that specifically binds scorpion venom polypeptide, including, but not limited to, ClC channel ligand-specific antibody and an ion channel polypeptide. The kits for detecting a ClC channel ligand-encoding polynucleotide include a moiety that specifically hybridizes to a ClC channel ligand-encoding polynucleotide. The kit may optionally provide additional components that are useful in the procedure, including, but not limited to, buffers, developing reagents, labels, reacting surfaces, means for detections, control samples, standards, instructions, and interpretive information.

Pharmaceutical kits for the treatment of scorpion stings, which include one or more containers containing a pharmaceutical composition including a therapeutically effective amount of a GaTx2 polypeptide inhibitor compound or antibody to a GaTx2 polypeptide. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The disclosure is further defined in the following Examples. It should be understood that these Examples, while indicating preferred embodiments, are given by way of illustration only, From the above discussion and these Examples, one skilled in the art can ascertain the essential characteristics of the various embodiments, and without departing from the spirit and scope thereof, can make various changes and modifications to adapt to various usages and conditions.

EXAMPLES

Example 1

Venom Preparation and Toxin Purification

Dried whole venom (Latoxan, France; or Sigma Chemical Co., Chicago, Ill.) was prepared at a stock concentration of 2 mg/mL in the appropriate bath solution (see below) for electrophysiological recording. The mucous portion of the venom was removed by processing the venom with four strokes in a Potter-Elvehjem tissue grinder, followed by centrifugation at 6000×g for 30 minutes to pellet the mucous component. The supernatant was passed through a 10 kDa molecular weight cut-off filter (Millipore Corp; Bedford, Mass.) by centrifugation at 2000×g for 40 minutes. The resulting partially fractionated venom (Lqh pf-venom) was then distributed into 1 mL aliquots and stored at −80° C. For RP-HPLC, venom was prepared at a concentration of 5 mg/mL in solution that contained (in mM): 150 NMDG-Cl, 5 $MgCl_2$, 10 TES, and 10 Tris•EGTA, pH 7.5.

Reversed-phase HPLC was performed on Lqh pf-venom prepared as described above. RP-HPLC was performed on a Waters 1525 binary HPLC coupled to a Waters 2487 dual wavelength absorbance detector, utilizing a Zorbax 300SB-C3 column (4.6 mm×250 mm) or Zorbax SB-C18 column (4.6 mm×250 mm).

Venom components were separated into fractions containing only components smaller than 10 kDa. Each fraction was tested for inhibition of ClC-2 currents using two-electrode voltage clamp (TEVC). With initial separation performed using a C3 column, the fraction collected from 0-10 minutes, Fraction A, retained activity similar to Lqh pf-venom (FIG. 1A, 45.7±6% inhibition, fraction concentration 0.1 mg/mL equivalent, n=3, p=0.01). The brief retention time of the active component on the C3 column suggests that the toxin is very hydrophilic.

Final isolation and purification of the active toxin was achieved through two successive rounds of RP-HPLC using a C18 column, as summarized in FIGS. 1B and 1C. The isolated toxin, peak #3, eluted at ~12 minutes and was sufficient to fully recapitulate the activity observed for Lqh pf-venom when diluted to the same equivalent concentration (64.2±5.3% inhibition at 0.1 mg/mL equivalent, n=4, p=0.025). Amino acid analysis performed during protein sequencing (see FIG. 2) revealed that this toxin was present at very low abundance, with 0.1 mg/mL venom containing this toxin at a concentration of only 10 nM. A preliminary dose-response curve constructed using native purified toxin showed that the $K_D$ at $V_M$=−160 mV is only 80 μM (FIG. 1D).

Example 2

Proteomic Characterization of GaTx2

The active toxin was analyzed via MALDI-MS at the Georgia Institute of Technology Bioanalytical Mass Spectrometry Facility. Edman degradation was performed at the Emory University Microchemical and Proteomics Facility. Sequence analysis of the natural and modified (reduced and alkylated) peptides was performed using Applied Biosystems model Procise-cLC automated protein sequencer (Applied Biosystems 491cLC CLC capillary protein sequencing system; Foster City, Calif.) using the manufacturer's cycles with slight modifications. Prior to sequencing, natural and modified samples were de-salted and purified via RP-HPLC.

Peak #3 was then subjected to MALDI-TOF mass spectrometric analysis to determine the molecular mass of the intact compound, and to ensure that the collected chromatographic peak contained only one component. This analysis revealed that peak #3 contained one component with an apparent mass of 3.19 kDa (FIG. 2A); a doubly charged species of the same component was also apparent.

Due to the lack of fragmentation of the intact toxin via MS/MS, Edman degradation was performed on the isolated toxin in order to obtain the primary sequence. Reduction of the active toxin with DTT followed by carboxamidomethylation induced a mass shift (3191.6 to 3539.5 kDa), as determined by MALDI-MS, that corresponded to the modification of 6 cysteine residues, indicating that the intact protein contained 3 disulfide linkages. The reduced/carboxamidomethylated toxin was then sequenced using Edman degradation and amino acid analysis, providing the complete primary sequence: [1]VSCEDCPDHCSTQKARAKCDNDKCV-CEPI[29] (SEQ ID NO: 1). The identity of the C-terminal residue, 129, was determined by amino acid analysis. This sequence was confirmed by Edman sequencing of Lys-C protease digested, reduced/carboxamidomethylated toxin. The toxin was isolated from venom on three separate occasions, as confirmed by MS analysis of the active fraction from these isolations. Sequence comparisons revealed that this primary sequence exactly matches the sequence of Leiuropeptide II (LPII), a peptide isolated in 1997 from the same scorpion which was not shown to have any lethal effects when injected into mouse brain or insects (Buisine, E. et al. (1997) *J. Pept. Res.* 49, 545-555). In fact, LPII was proposed to be a potassium channel inhibitor based on cysteine alignment and the presence of a lysine residue at position 18, which is in the same position in the folded protein as the critical lysine (Lys27) of charybdotoxin. Lysine 27 is part of a critical dyad, with its partner being an aromatic residue located ~6 Å away (Mouhat, S. et al. (2005) *J. Pept. Sci.* 11, 65-68). In LPII, however, this aromatic residue is absent. No target for LPII has ever been identified. Because this toxin actually inhibits a chloride channel, instead of a K⁺ channel as originally proposed, it was renamed to GaTx2 to avoid confusion. GaTx2 is also very similar in primary sequence to a number of other toxins; the most relevant are shown in FIG. 2B. Of these toxins, only four have been shown to be active against ion channels: neurotoxin P01, which is weakly toxic (Zerrouk, H. et al. (1996) *Int. J. Pept. Protein Res.* 48, 514-521), scyllatoxin, which inhibits $Ca^{2+}$-activated $K^+$ ($K_{Ca}$) channels (Chicchi, G. G. et al. (1988) *J. Biol. Chem.* 263, 10192-10197), and maurotoxin and OdK1, both of which inhibit Kv1.2 (Kharrat, R., et al. (1996) *European journal of biochemistry/FEBS* 242, 491-498) and (Abdel-Mottaleb, Y. et al. (2006) *FEBS Lett* 580, 6254-6258).

Example 3

Homology Model of GaTx2

A homology model of GaTx2 was created based on the neurotoxin P01 NMR structure (Blanc, E. et al. (1996) *Proteins* 24, 359-369) in order to make structural comparisons of GaTx2 to other known scorpion toxins (FIG. 2C middle). The homology model of GaTx2 was created using the Modeller 8v2 program, using neurotoxin P01 as the template structure. The GaTx2 homology model was then minimized via a 5 ps, 2500 step simulation with NAMDv2 utilizing the charmm22 force field. Prior to minimization, disulfide bridges were patched in order to ensure that the disulfide bonds remained intact during energy minimization.

This model predicts that GaTx2 is composed of 2 β-strands and one α-helix, which are connected via 3 disulfide bonds. This basic fold is highly conserved among numerous toxins isolated from various scorpion species (Rodriguez de la Vega, R. C. & Possani, L. D. (2004) *Toxicon* 43, 865-875).

GaTx2 is noticeably more compact than both scyllatoxin (FIG. 2C left) and chlorotoxin (FIG. 2C right), a toxin isolated from a related scorpion that is thought to inhibit an unidentified Cl⁻ channel in rat brain when reconstituted into lipid bilayers. The primary and secondary structures of GaTx2 are also very different from GaTx1, a recently isolated peptide inhibitor active against the CFTR Cl⁻ channel (Fuller, M. D., Thompson, C. H., Pohl, J., Kubanek, J., & McCarty, N. A. (2007) *Biophys. J.* 92 Supplement, 275a, Abstract, 1297-pos). GaTx2 is ~400 Da smaller than GaTx1 and has one fewer disulfide bond. GaTx2 has a calculated pI of just 4.51, which accounts for the large negative electrostatic potential that is associated with the protein and could possibly explain the lack of activity against cation channels.

Example 4

Inhibition of ClC-2 by Synthetic GaTx2

Figure 5A:
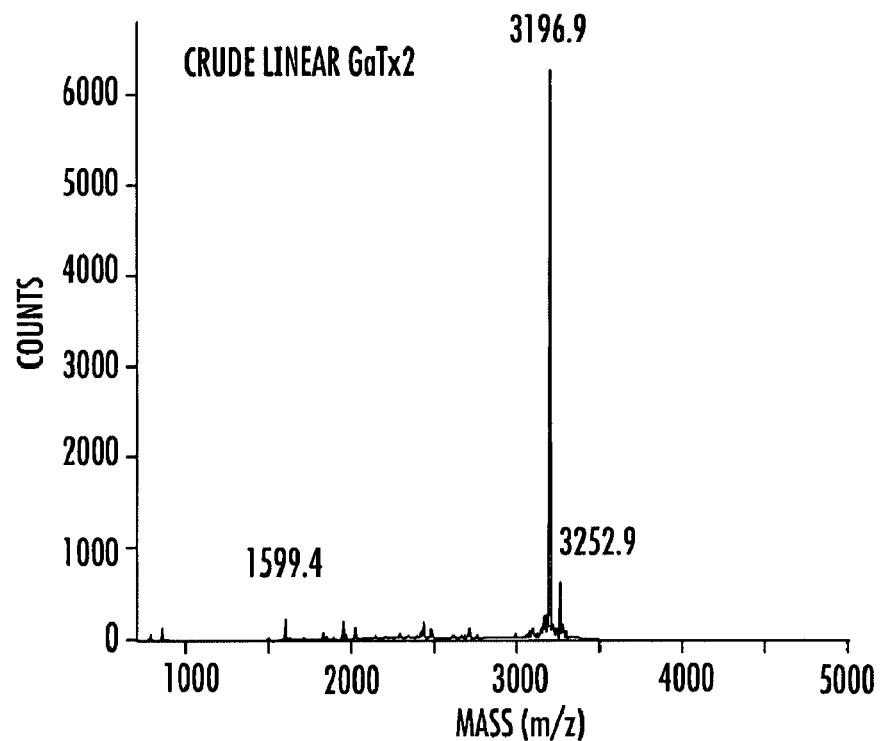
FIGS. 5A and 5B are line graphs showing that the folded synthetic toxin shows the same mass as the purified native toxin, indicating that no post-translational modifications were associated with the native toxin other than the three disulfide bonds.
Figure 5B:
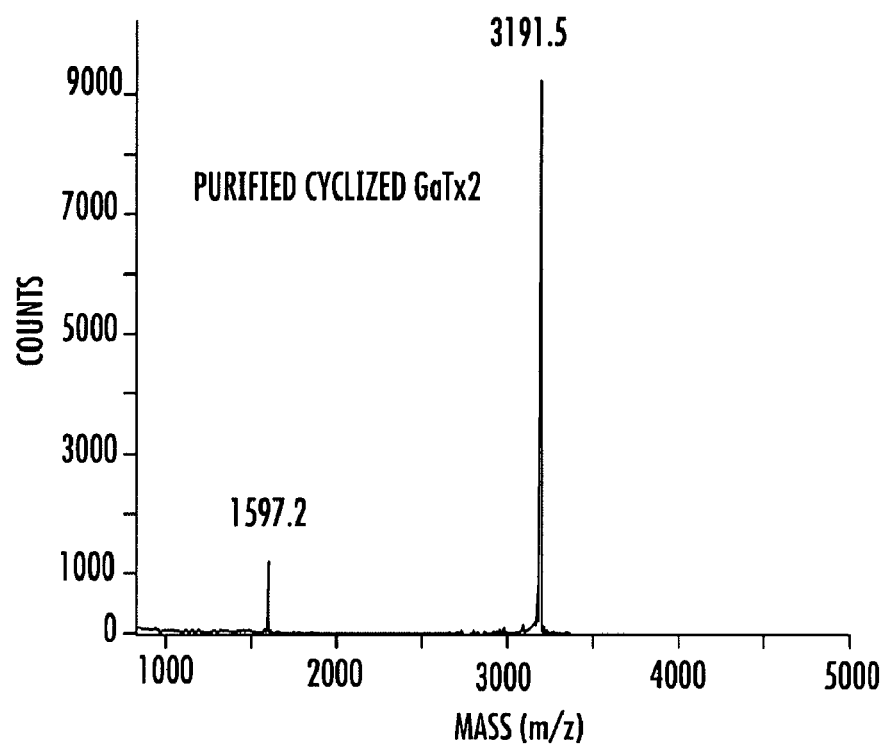

GaTx2 was produced via solid-phase chemical synthesis, as has been done for many other peptide inhibitors (Chang, N. S. et al. (1998) *Biochemistry* 37, 4407-4419; Hui, K. et al. (2003) *J. Gen. Physiol.* 122, 63-79). The folded synthetic toxin shows the same mass as the purified native toxin, indicating that no post-translational modifications were associated with the native toxin other than the three disulfide bonds (FIGS. 5A and B). Activity of synthetic GaTx2 was determined by recording from inside-out multi-channel patches.

Xenopus oocytes were isolated as previously described and incubated at 18° C. in a modified Liebovitz's L-15 medium (pH 7.5) with a cocktail of antibiotics (gentamicin, penicillin, streptomycin) and HEPES. CRNA was prepared from rabbit ClC-2 using a construct in pSport1, donated by H. C. Hartzell (Emory University, Atlanta, Ga.). For two-electrode voltage clamp experiments (TEYC), oocytes were injected with 2.5-25 ng of ClC-2 cRNA, 0.06-1 ng Sh13-IR cRNA, or 50-100 ng $GABA_C$-rho subunit cRNA. For patch recordings, oocytes were injected with 0.5-2 ng ClC-2 cRNA. Data were collected at room temperature 2-5 days post injection. Methods for animal handling are in accordance with the NIH guidelines and the protocol was approved by the Animal Use and Care Committee of the Georgia Institute of Technology.

Inside-out multi-channel and single channel patch clamp experiments were performed as previously described (Fuller, M. D. et al. (2005) Biophys. J. 89, 3960-3975). All data were recorded to DAT tape at 10 kHz and were subsequently filtered at 100 Hz and acquired by computer at 500 Hz. For inside-out patches in the presence of toxin, the toxin was backfilled into the pipette and allowed to diffuse to the surface of the patch. Unless otherwise stated, all single channel traces depicted in the figures were recorded at $V_M=-100$ mV. For all electrophysiological data shown, the horizontal dashed line indicates the zero-current level.

For experiments to construct a dose-response curve using inhibition of ClC-2 in excised, inside-out multi-channel patches, the pipette was backfilled with varying concentrations of synthetic toxin. The pipette was backfilled in such a way as to allow 10 minutes of control recording (at $V_M=-100$ mV or 60 mV), followed by 10 minutes of recording in the presence of GaTx2. The average window current from five separate four-minute windows in both control and experimental conditions was calculated.

When no toxin was backfilled into the pipette, no change in average window current over the course of the experiment was observed (FIG. 3A). However, when 2 nM synthetic GaTx2 was backfilled into the pipette average window currents were drastically reduced at the end of the experiment (FIG. 3A, B; 80.4±2.0% decrease). These experiments were repeated with varying concentrations of GaTx2 to obtain a dose-response curve, which provided $K_D=12$ pM and a Hill coefficient of 1.39 (FIG. 3B). This high affinity interaction is ~1 million times stronger than the best characterized inhibitors of ClC channels (Pusch, M. et al. (2000) Mol. Pharmacol. 58, 498-507).

Previous experiments with Lqh-pf venom indicated that inhibition of ClC-2 was voltage-dependent, with improved inhibitory efficacy at less hyperpolarizing potentials (Thompson, C. H. et al. (2005) J. Membr. Biol. 208, 65-76). The experiment shown in FIG. 1 provided a $K_D$ of 80 μM at $V_M=-160$ mV; in contrast, the experiments shown in FIG. 3 provided a $K_D$ Of 12 pM at $V_M=-100$ mV. This suggests that the binding affinity of GaTx2 is voltage-dependent. The degree of inhibition of ClC-2 current in multi-channel patches by 2 pM synthetic GaTx2 at $V_M=-100$ and −60 mV were determined (FIG. 3C). At $V_M=-100$ mV, 2 pM toxin did not inhibit ClC-2 (4.0±9.9% inhibition, n=11 windows); however, at $V_M=-60$ mV, ClC-2 currents were inhibited 41.4±4.1% (n=17 windows) by 2 μM toxin, confirming the notion that inhibition of ClC-2 by GaTx2 is voltage-dependent.

Example 5

Effect of GaTx2 on Single ClC-2 Channels

Peptide toxins may either inhibit channels by acting as pore blockers, which fully or partially occlude the pore, or by acting as gating modifiers, making it more difficult for the channel to open (McDonough, S. I. (2003) in Calcium Channel Pharmacology, ed. McDonough, S. I. Kluwer-Academic-Plenum Publishing, New York). In order to determine if GaTx2 alters the single channel conductance of ClC-2, all-points amplitude histograms were created from segments of records with only 1-2 open channels, in the absence and presence of GaTx2. In the presence of GaTx2, the single protopore amplitude at −100 mV was unchanged from control (0.25±0.01 pA vs, 0.26±0.01 pA, n 3, p=0.45) (FIG. 4A) as measured from the difference between O1 and O2 from the amplitude histograms created from 2-minute sections of record in the absence and presence of toxin. This suggests that GaTx2 does not induce partial conductances, although this does not discount the possibility of inhibition via a pore block mechanism.

Figure 4C:
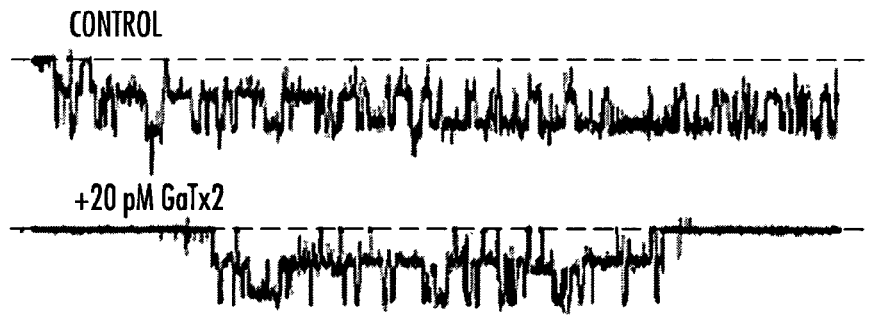
FIG. 4C shows an expanded single channel trace of a ClC-2 burst in the absence and presence of 20 pM GaTx2.
Figure 4D:
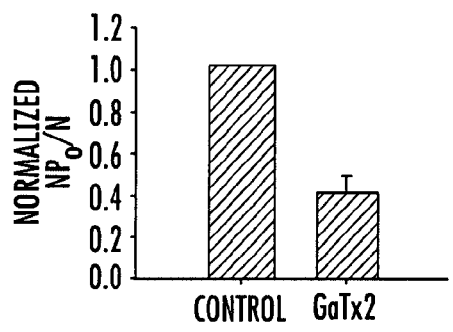
FIG. 4D is a bar graph showing a comparison of channel activity (as $NP_O/N$) in the absence and presence of 20 pM GaTx2.

Patch clamp experiments were performed with either one or two channels in the patch and 20 pM GaTx2 backfilled into the pipette. Measuring channel activity as $NP_O/N$, it was observed that $NP_O/N$ was reduced by 59.5±8% (FIG. 4D, n=2) at −100 mV, which is consistent with the reduction of window current observed in multichannel patches for this concentration of toxin (FIG. 3B). Some toxins act via a pore block mechanism by inducing long closed states within a channel burst. Expanded bursts (FIG. 4C) show that there appear to be no toxin-induced intraburst closures that would be consistent with a pore block mechanism.

Figure 4E:
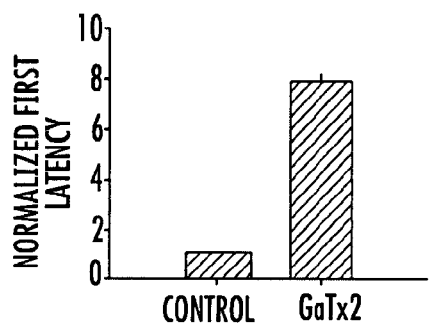
FIG. 4E is a bar graph showing a comparison of latency to opening of the first double-barreled burst after stepping from 0 to $-100$ mV, in the absence and presence of 20 pM GaTx2.

In the presence of 20 pM GaTx2, a 7.67±0.25 fold increase (FIG. 4E, n 2) in the latency to first opening upon stepping from $V_M0$ to −100 mV was observed, which is consistent with a modification of channel gating.

Example 6

Specificity of GaTx2

Peptide toxins are usually highly specific for their respective targets, although not always perfectly selective. Charybdotoxin (ChTx), for example, is known to inhibit both $K_{Ca}$, and $K_V$ channels. Because the GaTx2 sequence was originally predicted to be a K+ channel inhibitor, experiments were performed to determine if this toxin could inhibit the voltage-gated Drosophila Shaker K+ channel B variant with inactivation-removed (ShB-IR), by exposing oocytes expressing ShB-IR to 20 nM GaTx2, a concentration that strongly inhibits ClC-2 currents (FIG. 6A). No inhibition of ShB-IR currents was observed, indicating that GaTx2 does not interact with this channel, although the possibility remains that it may inhibit other K+ channels. Activity for GaTx2 against Kv1.2 K+ channels was tested by exposing oocytes expressing Kv1.2 channels to 10 nM GaTx2 (FIG. 6B). No inhibition of currents was observed for either peak currents or non-inactivating currents at this toxin concentration, which is 1000 fold greater than the $K_D$ for GaTx2 inhibition of ClC-2 channel currents.

Although ClC-2 is a very broadly expressed Cl− channel, many other Cl− channel types are expressed in excitable and non-excitable cells. Most inhibitors available for Cl− channels are very non-specific. Experiments were performed to determine whether GaTx2 is also capable of inhibiting currents from ligand-gated chloride channels formed by GABA$_C$ receptors, which are unrelated to ClC channels, GABA currents were measured both in the absence and presence of GaTx2 (FIG. 6C). Comparison of current in the presence of 10 μM GABA to currents in the presence of 10 μM GABA plus 10 nM GaTx2 showed no change (13±9.4% increase, p=0.32). GABA-induced Cl⁻ currents also did not increase upon removal of toxin from the bath solution (14±19% increase, p 0.74). This suggests that GaTx2 is not capable of inhibiting currents from GABA$_C$ receptors. This venom had no effect on the skeletal muscle Cl⁻ channel ClC-1. Experiments were performed to determine whether synthetic GaTx2 could inhibit ClC-1. Currents in the presence of toxin were compared to that after washout of toxin in order to account for channel rundown. In the presence of 10 nM GaTx2, tail currents at $V_M$=−120 mV from +60 mV were 1.036±0.012 fold larger than currents after washout of toxin, implying no inhibition of ClC-1 (FIG. 6D). 10 nM GaTx2 also did not inhibit ClC-3 channel mediated currents (FIG. 6E). Finally, inhibition of CFTR currents was determined by applying 60 nM cytoplasmically applied GaTx2 and using inside-out multi-channel channel patches. In the presence of GaTx2, normalized CFTR currents were 0.93±0.03 (n=10 windows, p 0.74) of control currents. Lqh pf-venom does not inhibit ClC-0 (Thompson, C. H. et al. (2005) *J. Membr. Biol.* 208, 65-76), and the fraction of venom that includes GaTx2 does not inhibit CFTR from the extracellular side (Fuller, M. D. et al (2004) *Am. J. Physiol.* 287, (C1328-C1341). This suggests that GaTx2 a specific ClC-2 channel inhibitor.

Example 7

GaTx2 Synthesis

Methods for peptide synthesis, purification, and folding have been previously described. Solid phase synthesis was performed by Fmoc chemistry, using the HBTU/HOBT/DIPEA method on an Applied Biosystems 431A synthesizer. Oxidative cyclization of the crude linear peptide was performed under equilibrating conditions. The cyclized peptide was then purified from the reaction mixture via RP-HPLC and characterized by MALDI-MS and analytical HPLC.

Statistics

Data are expressed as mean±SEM for n obervations. Differences were determined to be significant when p<0.05, using paired and unpaired Student's t-tests.

We claim:

1. A method for inhibiting activity of a ClC-2 channel in a subject comprising administering to the subject an isolated peptide having at least 95% sequence identity to SEQ ID NO:1, wherein the variation in amino acid sequence is due to a single conservative amino acid substitution, wherein the isolated peptide reduces chloride transport through the ClC-2 channel, and wherein the subject has diarrhea-predominant inflammatory bowel syndrome or secretory diarrhea.

2. The method of claim 1, wherein the isolated peptide has an apparent dissociation constant of about 12 pM for ClC-2 at −100 mV.

3. The method of claim 1, wherein the isolated peptide is approximately a 3.2 kDa peptide.

4. The method of claim 1, wherein the isolated peptide has a calculated pI of 4.51.

5. The method of claim 1, wherein the isolated peptide is synthetic or recombinant.

6. The method of claim 1, wherein the isolated peptide is administered in a dosage form.

7. The method of claim 1, wherein the isolated peptide is isolated from venom from *Leiurus quinquestriatus hebraeus*.

* * * * *

UNITED STATES PATENT AND TRADEMARK OFFICE
CERTIFICATE OF CORRECTION

PATENT NO. : 8,324,158 B2
APPLICATION NO. : 12/373556
DATED : December 4, 2012
INVENTOR(S) : Nael McCarty, Christopher H. Thompson and Julia Kubanek It is certified that error appears in the above-identified patent and that said Letters Patent is hereby corrected as shown below:

Cover sheet, (75) Inventors, replace "Neal McCarty" with --Nael McCarty--.

Signed and Sealed this
Twelfth Day of February, 2013

Teresa Stanek Rea
*Acting Director of the United States Patent and Trademark Office*

SEQUENCE LISTING

<160> NUMBER OF SEQ ID NOS: 12

<210> SEQ ID NO 1
<211> LENGTH: 29
<212> TYPE: PRT
<213> ORGANISM: Leiurus quinquestriatus hebraeus

<400> SEQUENCE: 1

Val Ser Cys Glu Asp Cys Pro Asp His Cys Ser Thr Gln Lys Ala Arg
1               5                   10                  15

Ala Lys Cys Asp Asn Asp Lys Cys Val Cys Glu Pro Ile
            20                  25

<210> SEQ ID NO 2
<211> LENGTH: 11
<212> TYPE: PRT
<213> ORGANISM: Human immunodeficiency virus

<400> SEQUENCE: 2

Tyr Gly Arg Lys Lys Arg Arg Gln Arg Arg Arg
1               5                   10

<210> SEQ ID NO 3
<211> LENGTH: 19
<212> TYPE: PRT
<213> ORGANISM: Drosophila melanogaster

<400> SEQUENCE: 3

Ser Gly Arg Gln Ile Lys Ile Trp Phe Gln Asn Arg Arg Met Lys Trp
1               5                   10                  15

Lys Lys Cys

<210> SEQ ID NO 4
<211> LENGTH: 19
<212> TYPE: PRT
<213> ORGANISM: Drosophila melanogaster

<400> SEQUENCE: 4

Ser Gly Arg Gln Ile Lys Ile Trp Phe Gln Asn Arg Arg Met Lys Trp

```
                        1               5                   10                  15
Lys Lys Cys

<210> SEQ ID NO 5
<211> LENGTH: 14
<212> TYPE: PRT
<213> ORGANISM: Human immunodeficiency virus

<400> SEQUENCE: 5

Ser Gly Tyr Gly Arg Lys Lys Arg Arg Gln Arg Arg Arg Cys
1               5                   10

<210> SEQ ID NO 6
<211> LENGTH: 29
<212> TYPE: PRT
<213> ORGANISM: Leiurus quinquestriatus hebraeus
<220> FEATURE:
<221> NAME/KEY: MISC_FEATURE
<222> LOCATION: (1)..(29)
<223> OTHER INFORMATION: Sequence from Leiuropeptide II

<400> SEQUENCE: 6

Val Ser Cys Glu Asp Cys Pro Asp His Cys Ser Thr Gln Lys Ala Arg
1               5                   10                  15

Ala Lys Cys Asp Asn Asp Lys Cys Val Cys Glu Pro Ile
            20                  25

<210> SEQ ID NO 7
<211> LENGTH: 29
<212> TYPE: PRT
<213> ORGANISM: Leiurus quinquestriatus hebraeus

<400> SEQUENCE: 7

Val Ser Cys Glu Asp Cys Pro Asp His Cys Ser Thr Gln Lys Ala Arg
1               5                   10                  15

Ala Lys Cys Asp Asn Asp Lys Cys Val Cys Glu Pro Lys
            20                  25

<210> SEQ ID NO 8
<211> LENGTH: 29
<212> TYPE: PRT
<213> ORGANISM: Unknown
<220> FEATURE:
<223> OTHER INFORMATION: Leuropeptide III

<400> SEQUENCE: 8

Val Ser Cys Glu Asp Cys Pro Glu His Cys Ser Thr Gln Lys Ala Gln
1               5                   10                  15

Ala Lys Cys Asp Asn Asp Lys Cys Val Cys Glu Pro Ile
            20                  25

<210> SEQ ID NO 9
<211> LENGTH: 29
<212> TYPE: PRT
<213> ORGANISM: Unknown
<220> FEATURE:
<223> OTHER INFORMATION: OdkI

<400> SEQUENCE: 9

Val Ser Cys Glu Asp Cys Pro Glu His Cys Ser Thr Gln Lys Ala Arg
1               5                   10                  15

Ala Lys Cys Asp Asn Asp Lys Cys Val Cys Glu Ser Val
            20                  25
```

```
<210> SEQ ID NO 10
<211> LENGTH: 28
<212> TYPE: PRT
<213> ORGANISM: Leiurus quinquestriatus hebraeus

<400> SEQUENCE: 10

Val Gly Cys Glu Glu Cys Pro Met His Cys Lys Gly Lys Asn Ala Lys
1               5                   10                  15

Pro Thr Cys Asp Asn Gly Val Cys Asn Cys Asn Val
            20                  25

<210> SEQ ID NO 11
<211> LENGTH: 34
<212> TYPE: PRT
<213> ORGANISM: Scorpio maurus palmatus

<400> SEQUENCE: 11

Val Ser Cys Thr Gly Ser Lys Asp Cys Tyr Ala Pro Cys Arg Lys Gln
1               5                   10                  15

Thr Gly Cys Pro Asn Ala Lys Cys Ile Asn Lys Ser Cys Lys Cys Tyr
            20                  25                  30

Gly Cys

<210> SEQ ID NO 12
<211> LENGTH: 31
<212> TYPE: PRT
<213> ORGANISM: Leiurus quinquestriatus hebraeus

<400> SEQUENCE: 12

Ala Phe Cys Asn Leu Arg Met Cys Gln Leu Ser Cys Arg Ser Leu Gly
1               5                   10                  15

Leu Leu Gly Lys Cys Ile Gly Asp Lys Cys Glu Cys Val Lys His
            20                  25                  30
```